(12) United States Patent
Akil et al.

(10) Patent No.: US 9,234,242 B2
(45) Date of Patent: Jan. 12, 2016

(54) METHODS FOR TREATING DEPRESSION USING NCAM PEPTIDE MIMETICS

(75) Inventors: Huda Akil, Ann Arbor, MI (US); Stanley J. Watson, Ann Arbor, MI (US); Cortney Turner, Belleville, MI (US); William E. Bunny, Laguna Hill, CA (US); Edward G. Jones, Winters, CA (US); Richard M. Myers, Stanford, CA (US); Alan F. Schatzberg, Los Altos, CA (US)

(73) Assignee: THE BOARD OF THE TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 13/431,893

(22) Filed: Mar. 27, 2012

(65) Prior Publication Data

US 2012/0277159 A1 Nov. 1, 2012

Related U.S. Application Data

(63) Continuation of application No. 12/093,437, filed as application No. PCT/US2006/044057 on Nov. 13, 2006.

(60) Provisional application No. 60/829,516, filed on Oct. 13, 2006, provisional application No. 60/736,526, filed on Nov. 12, 2005.

(51) Int. Cl.
*A61K 38/10* (2006.01)
*A61K 38/18* (2006.01)
*C12Q 1/68* (2006.01)
*A61K 38/17* (2006.01)
*G01N 33/50* (2006.01)
*A61K 38/03* (2006.01)

(52) U.S. Cl.
CPC .......... *C12Q 1/6883* (2013.01); *A61K 38/1774* (2013.01); *A61K 38/1825* (2013.01); *G01N 33/5023* (2013.01); *A61K 38/03* (2013.01); *A61K 38/10* (2013.01); *C12Q 2600/106* (2013.01); *C12Q 2600/136* (2013.01); *C12Q 2600/158* (2013.01); *G01N 2800/304* (2013.01)

(58) Field of Classification Search
CPC .... A61K 38/1774; A61K 38/10; A61K 38/03
See application file for complete search history.

(56) References Cited

U.S. PATENT DOCUMENTS

| | | | |
|---|---|---|---|
| 6,024,734 A | 2/2000 | Brewitt | |
| 6,342,478 B1 | 1/2002 | Frey, II | |
| 6,685,934 B1 | 2/2004 | Mallet et al. | |
| 7,309,687 B1 | 12/2007 | Brines et al. | |
| 2002/0169102 A1 | 11/2002 | Frey, II | |
| 2002/0192817 A1 | 12/2002 | Weiss et al. | |
| 2003/0096264 A1 | 5/2003 | Altar et al. | |
| 2003/0152972 A1 | 8/2003 | Sklar et al. | |
| 2003/0166555 A1 | 9/2003 | Alberini et al. | |
| 2003/0175253 A1 | 9/2003 | Akil et al. | |
| 2003/0191061 A1 | 10/2003 | Brewitt | |
| 2004/0152107 A1 | 8/2004 | Altar et al. | |
| 2004/0152111 A1 | 8/2004 | Akil et al. | |
| 2004/0242479 A1 * | 12/2004 | Bock et al. | 514/12 |
| 2006/0051786 A1 | 3/2006 | Akil et al. | |

FOREIGN PATENT DOCUMENTS

| | | |
|---|---|---|
| EP | 1233075 A2 | 8/2002 |
| EP | 1 586 657 A1 | 10/2005 |
| WO | WO 94/12201 A1 | 6/1994 |
| WO | WO 95/26409 A1 | 10/1995 |
| WO | WO 97/34618 A1 | 9/1997 |
| WO | WO 99/15697 A1 | 4/1999 |
| WO | WO 99/62522 A1 | 12/1999 |
| WO | WO 00/42173 A1 | 7/2000 |
| WO | WO 02/057790 A2 | 7/2002 |
| WO | WO 2004/043395 A2 | 5/2004 |
| WO | WO 2004/047727 A2 | 6/2004 |
| WO | WO 2005/014623 A2 | 2/2005 |
| WO | WO 2005014623 A2 * | 2/2005 |
| WO | WO 2005/046434 A2 | 5/2005 |
| WO | WO 2006/002262 A2 | 1/2006 |

OTHER PUBLICATIONS

Bipolar disorder fact sheet, PubMed Health, NLM, NIH, pp. 1-5, retrieved Oct. 16, 2012.*
Starkstein, SE et al. (2005) The construct of minor and major depression in Alzheimer's disease. Am. J. Psychiatry, 162:2086-2093.*
Yan et al. (2000) Two-amino acid molecular switch in an epithelial morphogen that regulates binding to two distinct receptors. Science, 290(5491):523-527.*
Zhu et al. (1995) Glu-96 of basic fibroblast growth factor is essential for high affinity receptor binding. J. Biol Chem. 270(37):21869-21874.*
Zubenko GS et al. (2003) A collaborative study of the emergence and clinical features of the major depressive syndrome of Alzheimer's disease. Am. J. Psychiatry, 160:857-866.*
Kempermann G & Kronenberg G. (2003) Depressed new neurons?—Adult hippocampal neurogenesis and a cellular plasticity hypothesis of major depression. Biol. Psychiatry, 54:499-503.*

(Continued)

*Primary Examiner* — Kimberly A. Ballard
(74) *Attorney, Agent, or Firm* — Kilpatrick Townsend & Stockton LLP

(57) ABSTRACT

The present application relates to the treatment and diagnosis of mood disorders, including bipolar disorder, major depression disorder and schizophrenia. The invention provides novel diagnostic markers and assays, as well as research tools for the development and discovery of agents and compounds which are useful for treating patients who suffer from mental illness.

11 Claims, 11 Drawing Sheets

(56) References Cited

OTHER PUBLICATIONS

Gray TE et al. (1996) Asparagine-344 is a key residue for ligand binding in keratinocyte growth factor receptor. Biochem. 35:15640-15645.*
Belluardo et al. "Central nicotinic receptors, neurotrophic factors and neuroprotection," Behav. Brain Res. Aug. 2000; 113(1-2):21-34.
Bezchlibnyk et al. "Gene expression differences in bipolar disorder revealed by cDNA array analysis of post-mortem frontal cortex," Journal of Neurochemistry, 2001, vol. 79, pp. 826-834.
Brown, T.A. et al., "Current and Lifetime Comorbidity of the DSM-IV Anxiety and Mood Disorders in a Large Clinical Sample," Journal of Abnormal Psychology, 2001, vol. 110, No. 4, pp. 585-599.
Bunney et al. "Microarray Technology: A Review of New Strategies to Discover Candidate Vulnerability Genes in Psychiatric Disorders," Am J Psychiatry, 2003, vol. 160, pp. 657-666.
Chen et al. "Discordant Protein and mRNA Expression in Lung Adenocarcinomas*," Molecular & Cellular Proteomics, 2002, vol. 1, pp. 304-313.
El-Husseini et al. "Basic fibroblast growth factor (BFGF) and two of its receptors, FGFR1 and FGFR2: gene expression in the rat brain during postnatal development as determined by quantitative RT-PCR," Molecular and Cellular Endocrinology, 1994, vol. 104, pp. 191-200.
Evans et al. "Dysregulation of the fibroblast growth factor system in major depression," PNAS, 2004, vol. 101, No. 43, pp. 15506-15511.
Fatemi et al. "Altered levels of Reelin and its isoforms in schizophrenia and mood disorders," NeuroReport, Oct. 29, 2001, vol. 12, No. 15, pp. 3209-3215.
Gaughran et al. "Hippocampal FGF-2 and FGFR1 mRNA expression in major depression, schizophrenia and bipoloar disorder," Brain Research Bulletin, 2006, vol. 70, pp. 221-227.
Gomez-Pinilla et al. "Basic FGF in Adult Rat Brain: Cellular Distribution and Response to Entorhinal Lesion and Fimbria-Fornix Transection." J Neurosci., 1992, vol. 12, No. 1, pp. 345-355.
Gomez-Pinilla et al. "Diazepam induces FGF-2 mRNA in the hippocampus and striatum," Brain Research Bulletin, 2000, vol. 53, No. 3, pp. 283-289.
Grimes et al., "Cholinergic Stimulation of Early Growth Response-1 DNA Binding Activity Requires Protein Kinase C and Mitogen-Activated Protein Kinase Kinase Activation and is Inhibited by Sodium Valproate in SH-SY5Y Cells," J. Neurochem., 1999, vol. 73, No. 4, pp. 1384-1392.
Haynes et al., "Protein Analysis: Biological Assay or Data Archive?" Electrophoresis, 1998, vol. 19, pp. 1862-1871.
Heiskanen et al., "CGH, cDNA and tissue microarray analyses Implicate FGFR2 amplification in a small subset of breast tumors," Analytical Cellular Pathology, 2001, vol. 22, No. 4, pp. 229-234.
Herdegen et al., "JUN, FOS, KROX, and CREB Transcription Factor Proteins in the Rat Cortex: Basal Expression and Induction by Spreading Depression and Epileptic Seizures," J. Comparative Neurology, 1993, vol. 333, No. 2, pp. 271-288.
Knable et al. "Multivariate analysis of prefrontal cortical data from the Stanley Foundation Neuropathology Consortium," Brain Research Bulletin, 2001, vol. 55, No. 5, pp. 651-659.
Knuuttila, Juha E.A. et al., "Effects of antidepressant drug imipramine on gene expression in rat prefrontal cortex," Neurochemical Research, Jun. 1, 2004, vol. 29, No. 6, pp. 1235-1244.
Kuromitsu et al. "Reduced neuropeptide Y mRNA levels in the frontal cortex of people with schizophrenia and bipolar disorder," Gene Expression Patterns, 2001, pp. 17-21.
Landgrebe, J., et al., "Molecular characterization of antidepressant effect in the mouse brain using gene expression profiling," J. Psychiatric Res, Elsevier Ltd., GB, vol. 36, No. 3, May 1, 2002, pp. 119-129.
Mallei et al., "Antidepressant Treatments Induce the Expression of Basic Fibroblast Growth Factor in Cortical and Hippocampal Neurons," Molecular Pharmacology, 2002, vol. 61, No. 5, pp. 1017-1024.
Mickle et al. "Genotype-phenotype relationships in cystic fibrosis," Med Clin. North Am., 2000, vol. 84, No. 3, pp. 597-607.
Mills et al. "DNA microarrays and beyond: completing the journey from tissue to cell," Nature Cell Biology, 2001, vol. 3, pp. E175-E178.
NCBI accession AB030073, downloaded Jul. 2, 2007.
NCBI accession AB030074, downloaded Jul. 2, 2007.
NCBI accession AB030075, downloaded Jul. 2, 2007.
NCBI Gene ID:2263, download Jul. 2, 2007.
Nechifor 2007 (Magnesium in Psychoses, Chapter 30 un New Perspectives in Magnesium Research, pp. 369-377).
Newton, Samuel S. et al., "Regulation of Neurogenesis and Angiogenesis in Depression," Current Neurovascular Research, 2004, vol. 1, pp. 261-267.
Ovalle et al. "Fibroblast growth factor-2 is selectively modulated in the rat brain by E-5842, a preferential sigma-1 receptor ligand and putative atypical antipsychotic," European Journal of Neuroscience, 2001, vol. 13, pp. 909-915.
Sabban et al., "Differential Effects of Stress on Gene Transcription Factors in Catecholaminergic Systems," Ann. N.Y. Acad. Sci., 2004, vol. 1032, pp. 130-140.
Turner et al., "Antidepressant-like Effects of Intracerebroventricular FGF2 in Rats," Brain Research, 2008, vol. 1224, pp. 63-68.
Vawter et al., "Microarray Screening of Lymphocyte Gene Expression Differences in a Multiplex Schizophrenia Pedigree," Schizophrenia Research, 2004, vol. 67, pp. 41-52.
Voet et al. Biochemistry. 1990. John Wiley & Sons, Inc. 126-129 and 228-234.
Wagner, et al., "Stimulation of Neonatal and Adult Brain Neurogenesis by Subcutaneous Injection of Basic Fibroblast Growth Factor," J. Neurosci, 1999; vol. 19, No. 14, pp. 6006-6016.
Yan et al. "Two-amino acid molecular switch in an epithelial morphogen that regulates binding to two distinct receptors," Science, 2000, vol. 290, pp. 523-527.
Zhu et al., "Glu-96 of Basic Fibroblast Growth Factor is Essential for High Affinity Receptor Binding," J Biol. Chem., 1995; vol. 270, vol. 37, pp. 21869-21874.

* cited by examiner

FIG. 4
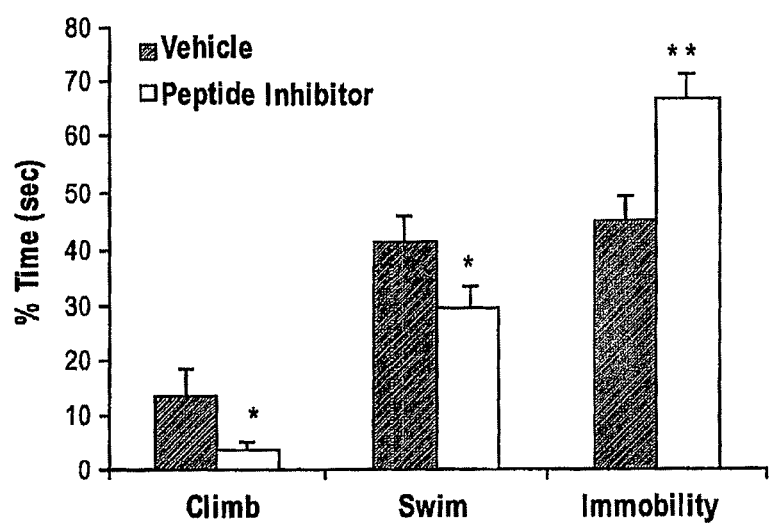
FST
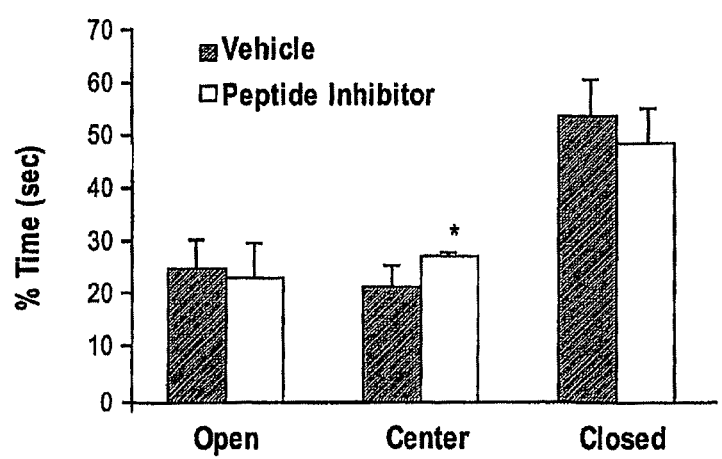
EPM

Dysregulation of genes involved in cAMP signaling pathways in AnCg from patients with BPD

| Symbol | Name | UniGene ID | Cytoband | U95Av2 | U133A |
|---|---|---|---|---|---|
| NPY1R | Neuropeptide Y receptor Y1 | Hs.519057 | 4q31-q32 | | 24.4** |
| NPY | Neuropeptide Y | Hs.1832 | 7p15 | 22.1** | 33.0** |
| SST | Somatostatin | Hs.12409 | 3q28 | 29.0** | 22.1** |
| GRM3 | Metabotropic Glutamate receptor 3 | Hs.112621 | 7q21 | 33.4* | 34.4* |
| EDG2 | Endothelial differentiation GPCR 2 | Hs.126667 | 9q31.3 | 24.1* | 18.2* |
| GNAI1 | G protein alpha inhibiting activity 1 | Hs.134587 | 7q21 | 40.4** | |
| PDE1A | Phosphodiesterase 1A | Hs.416061 | 2q32 | 20.1** | 24.1** |
| PDE8A | Phosphodiesterase 8A | Hs.9333 | 15q25 | 16.3* | 12.5* |
| PKIA | Protein kinase A inhibitor alpha | Hs.433700 | 8q21 | 14.2* | 16.6* |
| CDK5 | Cyclin-dependent kinase 5 | Hs.166071 | 7q36 | 10.5* | 12.0* |
| PPP1CA | Protein phosphatase 1, catalytic alpha | Hs.183994 | 11q13 | 13.1* | 16.8* |

**The p-values showing a false discovery rate (FDR) of less than 5%
* p-value of less than 0.05 regardless of FDR The probability that the group of molecules that act negatively on cAMP signaling activity are detected as genes increased in BPD by chance, based on a hypergeometric distribution, was p = 0.037 (q = 0.36).

Dysregulation of genes involved in cAMP signaling pathways in AnCg from patients with MDD

| Symbol | Name | UniGene ID | Cytoband | MDD Cohort A | | | MDD Cohort B |
|---|---|---|---|---|---|---|---|
| | | | | U95Av2 | U133A | U133A | U133A |
| PDE8A | Phosphodiesterase 8A | Hs.9333 | 15q25 | -24.3** | -23.1** | -17.8* |
| RGS20 | Regulator of G-protein signalling 20 | Hs.368733 | 8q12 | -28.2** | -29.2** | -13.9* |
| EDG1 | Endothelial differentiation GPCR 1 | Hs.154210 | 1p21 | -19.7* | -21.2** | -10.4* |
| PPP1R3C | Protein phosphatase 1, regulatory 3C | Hs.303090 | 10q23-q24 | -35.4** | -63.2** | -21.4** |

**The p-values showing a false discovery rate (FDR) of less than 5%
* p-value of less than 0.05 regardless of FDR

FIG. 7

Dysregulation of genes involved in phosphatidylinositol signalling pathways in AnCg from patients with BPD

| Symbol | Name | UniGene ID | Cytoband | U95Av2 | U133A |
|---|---|---|---|---|---|
| EDG2 | Endothelial differentiation GPCR 2 | Hs.126667 | 9q31.3 | 24.1* | 18.2* |
| ITPKB | Inositol 1,4,5-trisphosphate 3-kinase B | Hs.528087 | 1q41-q43 | 14.8* | 11.5* |
| INPP1 | Inositol polyphosphate-1-phosphatase | Hs.32309 | 2q32 | 21.5** | 24.9** |
| CDS1 | CDP-diacylglycerol synthase 1 | Hs.444924 | 4q21.23 | -29.5** | -24.2* |
| PIK3C2A | Phosphoinositide-3-kinase catalytic 2A | Hs.175343 | 11p15-p14 | | 22.3** |
| PIK3C2B | Phosphoinositide-3-kinase catalytic 2B | Hs.497487 | 1q32 | 16.6* | 14.8* |
| PIK3R1 | Phosphoinositide-3-kinase regulatory 1 | Hs.132225 | 5q13 | -32.0** | |
| PRKCI | Protein kinase C (iota) | Hs.478199 | 3p25-q27 | -29.5** | |

*** The p-values showing a false discovery rate (FDR) of less than 5%
* p-value of less than 0.05 regardless of FDR The probability that the group of the phosphatidylinositol 3-kinases are detected by chance as differentially expressed genes in the comparison between BPD and control, based on a hypergeometric distribution, was $p = 0.042$ ($q = 0.36$).

FIG. 8

Dysregulation of genes involved in phosphatidylinositol signalling pathways in AnCg from patients with MDD

| Symbol | Name | UniGene ID | Cytoband | MDD Cohort A | | | MDD Cohort B |
|---|---|---|---|---|---|---|---|
| | | | | U95Av2 | U133A | | U133A |
| NTSR2 | Neurotensin receptor 2 | Hs.131138 | 2p25.1 | -13.9* | -18.6* | | -24.7** |
| EDNRB | Endothelin receptor type B | Hs.82002 | 13q22 | | -31.2** | | -15.9* |
| ITPKB | Inositol 1,4,5-trisphosphate 3-kinase B | Hs.528087 | 1q41-q43 | -12.7* | -12.3* | | -34.0** |
| INPP5F | Inositol polyphosphate-5-phosphatase F | Hs.369755 | 10q26 | | 21.8** | | |
| ITPR1 | Inositol 1,4,5-triphosphate receptor 1 | Hs.374613 | 3p26-p25 | 13.0* | 17.4* | | |
| PRKCB1 | Protein kinase C beta 1 | Hs.460355 | 16p11 | 14.8* | 11.5* | | |
| PIK3C2A | Phophoinositide-3-kinase catalytic 2A | Hs.175343 | 11p15-p14 | -14.1* | -35.9** | | -20.2* |

**The p-values showing a false discovery rate (FDR) of less than 5%
* p-value of less than 0.05 regardless of FDR Correlation Coefficient= .77; P<003.

FIG. 11

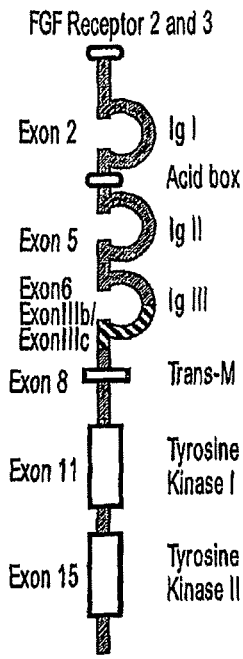

FGFR2 and FGFR3 Primer Sequences

| Amplicon | Primer | Sequence | Primer | Sequence |
|---|---|---|---|---|
| Exon 2 | R2 F | 5'-GCCGTGATCAGTTGGACTAAG-3' | R3 F | 5'-AGAGGCTTCAAGTGCTAAACG-3' |
|  | R2 R | 5'-TGTGGCACCTTTTATCTGGAG-3' | R3 R | 5'-GCACACTAAAGTGGCACAGC-3' |
| Exon 5 | R2 F | 5'-TATGGAAAGTGTGGTCCCATC-3' | R3 F | 5'-TGGAGCTTGGTCATGGAAAG-3' |
|  | R2 R | 5'-ACATCAAGGTGGTAGGTGTGG-3' | R3 R | 5'-GGATGCTGCCAAACTTGTTC-3' |
| Exon 6 | R2 F | 5'-GGAGGGGACGTAGAATTTGTC-3' | R3 F | 5'-CCAACCAGACAGCCGTTC-3' |
|  | R2 R | 5'-CTTCAGGACCTTGAGGTAGGG-3' | R3 R | 5'-CATTCACCTCCACGTGCTT-3' |
| Exon IIIb | R2 F | 5'-GGGGATAAATAGCTCCAATGC-3' | R3 F | 5'-CCTGGATCAGTGAGAATGTGG-3' |
|  | R2 R | 5'-CATATATATTCCCCAGCATCCATC-3' | R3 R | 5'-AAATTGGTGGCTCGACAGAG-3' |
| Exon IIIc | R2 F | 5'-ACACCACGGACAAAGAAATTG-3' | R3 F | 5'-TGTCCTTGCACAATGTCACC-3' |
|  | R2 R | 5'-ATAGAATTACCCGCCAAGCAC-3' | R3 R | 5'-ACGCAGAGTGATGGGAAAAC-3' |
| Exon 8 | R2 F | 5'-GATCACAGCTTCCCCAGATTAC-3' | R3 F | 5'-GGAGGAGCTGATGGAAGTTG-3' |
|  | R2 R | 5'-TCTTGGTCGTGGTCTTCATTC-3' | R3 R | 5'-CCACCAGGATGAAGAGGAAG-3' |
| Exon 11 | R2 F | 5'-AGAGAAGGACCTGTCTGACCTG-3' | R3 F | 5'-ATGCCACTGACAAGGACCTG-3' |
|  | R2 R | 5'-CCCAGGAGGTTGATGATGTTC-3' | R3 R | 5'-CCCCCAACAGGTTAATGATG-3' |
| Exon 15 | R2 F | 5'-GTCCTTCGGGGTGTTAATGTG-3' | R3 F | 5'-TCCTTTGGTGTCCTCCTCTG-3' |
|  | R2 R | 5'-AGTTCATTGGTGCAGTTGGTG-3' | R3 R | 5'-CAGTTGGCTGGCTTGTCC-3' |

FIG. 12
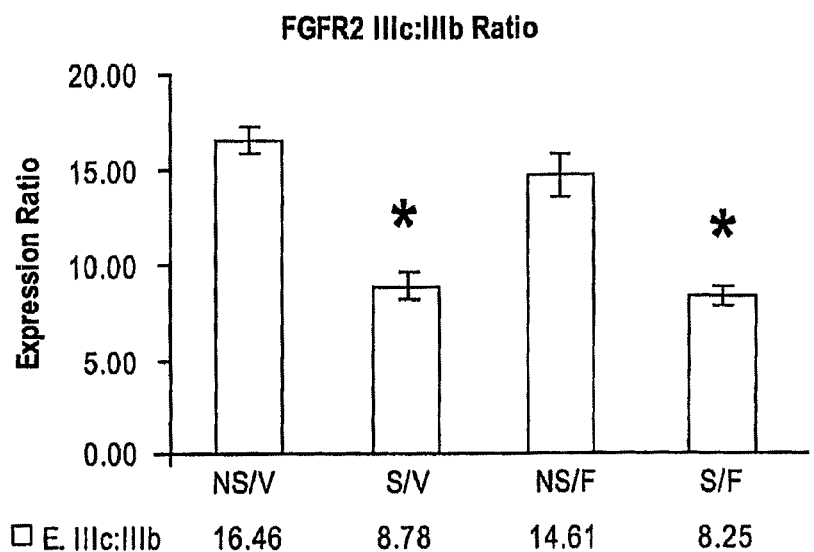
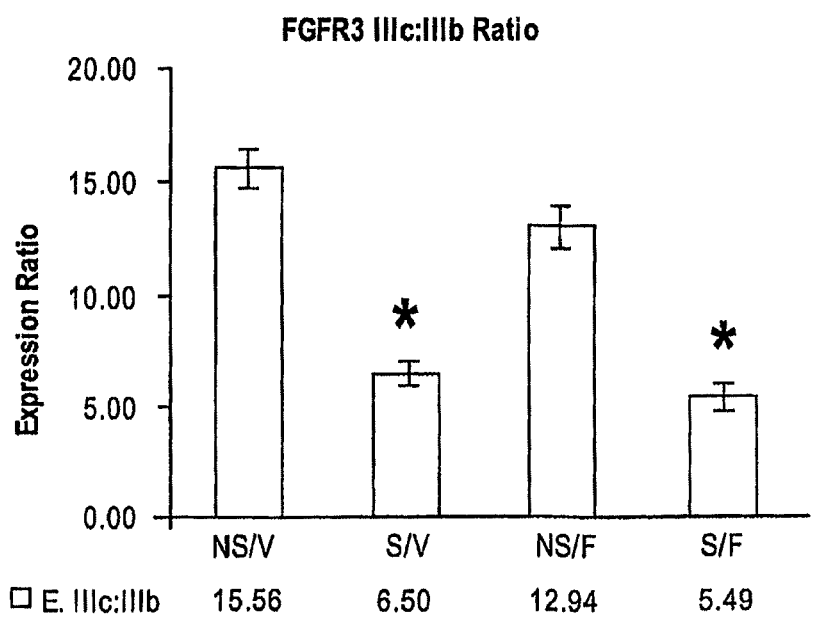

```
                        SEQUENCE LISTING

<160> NUMBER OF SEQ ID NOS: 35

<210> SEQ ID NO 1
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 2 amplicon real time reverse-transcriptase-PCR amplification
      forward primer R2 F

<400> SEQUENCE: 1
gccgtgatca gttggactaa g                                             21

<210> SEQ ID NO 2
<211> LENGTH: 21
<212> TYPE: DNA
<213> ORGANISM: Artificial Sequence
<220> FEATURE:
<223> OTHER INFORMATION: fibroblast growth factor receptor 3 (FGFR3)
      exon 2 amplicon real time reverse-transcriptase-PCR amplification
      forward primer R3 F

<400> SEQUENCE: 2
agaggcttca agtgctaaac g                                             21

<210> SEQ ID NO 3
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 2 amplicon real time reverse-transcriptase-PCR amplification
      reverse primer R2 R

<400> SEQUENCE: 3
tgtggcacct tttatctgga g                                             21

<210> SEQ ID NO 4
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 2 amplicon real time reverse-transcriptase-PCR amplification
      reverse primer R3 R
```

```
<400> SEQUENCE: 4
gcacactaaa gtggcacagc                                              20

<210> SEQ ID NO 5
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 5 amplicon real time reverse-transcriptase-PCR amplification
      forward primer R2 F

<400> SEQUENCE: 5
tatggaaagt gtggtcccat c                                            21

<210> SEQ ID NO 6
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 5 amplicon real time reverse-transcriptase-PCR amplification
      forward primer R3 F

<400> SEQUENCE: 6
tggagcttgg tcatggaaag                                              20

<210> SEQ ID NO 7
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 5 amplicon real time reverse-transcriptase-PCR amplification
      reverse primer R2 R

<400> SEQUENCE: 7
acatcaaggt ggtaggtgtg g                                            21

<210> SEQ ID NO 8
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 5 amplicon real time reverse-transcriptase-PCR amplification
      reverse primer R3 R

<400> SEQUENCE: 8
ggatgctgcc aaacttgttc                                              20

<210> SEQ ID NO 9
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 6 amplicon real time reverse-transcriptase-PCR amplification
      forward primer R2 F

<400> SEQUENCE: 9
ggaggggacg tagaatttgt c                                            21

<210> SEQ ID NO 10
<211> LENGTH: 18
<212> TYPE: DNA
<213> ORGANISM: Artificial Sequence
```

```
<220> FEATURE:
<223> OTHER INFORMATION: fibroblast growth factor receptor 3 (FGFR3)
      exon 6 amplicon real time reverse-transcriptase-PCR amplification
      forward primer R3 F

<400> SEQUENCE: 10
ccaaccagac agccgttc                                                    18

<210> SEQ ID NO 11
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 6 amplicon real time reverse-transcriptase-PCR amplification
      reverse primer R2 R

<400> SEQUENCE: 11
cttcaggacc ttgaggtagg g                                                21

<210> SEQ ID NO 12
<211> LENGTH: 19
<212> TYPE: DNA
<213> ORGANISM: Artificial Sequence
<220> FEATURE:
<223> OTHER INFORMATION: fibroblast growth factor receptor 3 (FGFR3)
      exon 6 amplicon real time reverse-transcriptase-PCR amplification
      reverse primer R3 R

<400> SEQUENCE: 12
cattcacctc cacgtgctt                                                   19

<210> SEQ ID NO 13
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon IIIb amplicon real time reverse-transcriptase-PCR
      amplification forward primer R2 F

<400> SEQUENCE: 13
ggggataaat agctccaatg c                                                21

<210> SEQ ID NO 14
<211> LENGTH: 21
<212> TYPE: DNA
<213> ORGANISM: Artificial Sequence
<220> FEATURE:
<223> OTHER INFORMATION: fibroblast growth factor receptor 3 (FGFR3)
      exon IIIb amplicon real time reverse-transcriptase-PCR
      amplification forward primer R3 F

<400> SEQUENCE: 14
cctggatcag tgagaatgtg g                                                21

<210> SEQ ID NO 15
<211> LENGTH: 24
<212> TYPE: DNA
<213> ORGANISM: Artificial Sequence
<220> FEATURE:
<223> OTHER INFORMATION: fibroblast growth factor receptor 2 (FGFR2)
      exon IIIb amplicon real time reverse-transcriptase-PCR
      amplification reverse primer R2 R

<400> SEQUENCE: 15
catatatatt ccccagcatc catc                                             24
```

```
<210> SEQ ID NO 16
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon IIIb amplicon real time reverse-transcriptase-PCR
      amplification reverse primer R3 R

<400> SEQUENCE: 16
aaattggtgg ctcgacagag                                                   20

<210> SEQ ID NO 17
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon IIIc amplicon real time reverse-transcriptase-PCR
      amplification forward primer R2 F

<400> SEQUENCE: 17
acaccacgga caaagaaatt g                                                 21

<210> SEQ ID NO 18
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon IIIc amplicon real time reverse-transcriptase-PCR
      amplification forward primer R3 F

<400> SEQUENCE: 18
tgtccttgca caatgtcacc                                                   20

<210> SEQ ID NO 19
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon IIIc amplicon real time reverse-transcriptase-PCR
      amplification reverse primer R2 R

<400> SEQUENCE: 19
atagaattac ccgccaagca c                                                 21

<210> SEQ ID NO 20
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon IIIc amplicon real time reverse-transcriptase-PCR
      amplification reverse primer R3 R

<400> SEQUENCE: 20
acgcagagtg atgggaaaac                                                   20

<210> SEQ ID NO 21
<211> LENGTH: 22
<212> TYPE: DNA
<213> ORGANISM: Artificial Sequence
<220> FEATURE:
<223> OTHER INFORMATION: fibroblast growth factor receptor 2 (FGFR2)
      exon 8 amplicon real time reverse-transcriptase-PCR amplification
      forward primer R2 F
```

<400> SEQUENCE: 21
gatcacagct tccccagatt ac                                              22

<210> SEQ ID NO 22
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 8 amplicon real time reverse-transcriptase-PCR amplification
      forward primer R3 F

<400> SEQUENCE: 22
ggaggagctg atggaagttg                                                 20

<210> SEQ ID NO 23
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 8 amplicon real time reverse-transcriptase-PCR amplification
      reverse primer R2 R

<400> SEQUENCE: 23
tcttggtcgt ggtcttcatt c                                               21

<210> SEQ ID NO 24
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 8 amplicon real time reverse-transcriptase-PCR amplification
      reverse primer R3 R

<400> SEQUENCE: 24
ccaccaggat gaagaggaag                                                 20

<210> SEQ ID NO 25
<211> LENGTH: 22
<212> TYPE: DNA
<213> ORGANISM: Artificial Sequence
<220> FEATURE:
<223> OTHER INFORMATION: fibroblast growth factor receptor 2 (FGFR2)
      exon 11 amplicon real time reverse-transcriptase-PCR amplification
      forward primer R2 F

<400> SEQUENCE: 25
agagaaggac ctgtctgacc tg                                              22

<210> SEQ ID NO 26
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 11 amplicon real time reverse-transcriptase-PCR amplification
      forward primer R3 F

<400> SEQUENCE: 26
atgccactga caaggacctg                                                 20

<210> SEQ ID NO 27
<211> LENGTH: 21
<212> TYPE: DNA

```
<213> ORGANISM: Artificial Sequence
<220> FEATURE:
<223> OTHER INFORMATION: fibroblast growth factor receptor 2 (FGFR2)
      exon 11 amplicon real time reverse-transcriptase-PCR amplification
      reverse primer R2 R

<400> SEQUENCE: 27
cccaggaggt tgatgatgtt c                                              21

<210> SEQ ID NO 28
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 11 amplicon real time reverse-transcriptase-PCR amplification
      reverse primer R3 R

<400> SEQUENCE: 28
cccccaacag gttaatgatg                                                20

<210> SEQ ID NO 29
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 15 amplicon real time reverse-transcriptase-PCR amplification
      forward primer R2 F

<400> SEQUENCE: 29
gtccttcggg gtgttaatgt g                                              21

<210> SEQ ID NO 30
<211> LENGTH: 20
<212> TYPE: DNA
<213> ORGANISM: Artificial Sequence
<220> FEATURE:
<223> OTHER INFORMATION: fibroblast growth factor receptor 3 (FGFR3)
      exon 15 amplicon real time reverse-transcriptase-PCR amplification
      forward primer R3 F

<400> SEQUENCE: 30
tcctttggtg tcctcctctg                                                20

<210> SEQ ID NO 31
<211> LENGTH: 21
<212> TYPE: DNA
<213> ORGANISM: Artificial Sequence
<220> FEATURE:
<223> OTHER INFORMATION: fibroblast growth factor receptor 2 (FGFR2)
      exon 15 amplicon real time reverse-transcriptase-PCR amplification
      reverse primer R2 R

<400> SEQUENCE: 31
agttcattgg tgcagttggt g                                              21

<210> SEQ ID NO 32
<211> LENGTH: 18
<212> TYPE: DNA
<213> ORGANISM: Artificial Sequence
<220> FEATURE:
<223> OTHER INFORMATION: fibroblast growth factor receptor 3 (FGFR3)
      exon 15 amplicon real time reverse-transcriptase-PCR amplification
      reverse primer R3 R

<400> SEQUENCE: 32
cagttggctg gcttgtcc                                                  18
```

```
<210> SEQ ID NO 33
<211> LENGTH: 200
<212> TYPE: PRT
<213> ORGANISM: Artificial Sequence
<220> FEATURE:
<223> OTHER INFORMATION: poly-Gly flexible linker
<220> FEATURE:
<221> NAME/KEY: MOD_RES
<222> LOCATION: (6)...(200)
<223> OTHER INFORMATION: Xaa = Gly or absent

<400> SEQUENCE: 33

Gly Gly Gly Gly Gly Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
                180                 185                 190

Xaa Xaa Xaa Xaa Xaa Xaa Xaa Xaa
            195                 200

<210> SEQ ID NO 34
<211> LENGTH: 15
<212> TYPE: PRT
<213> ORGANISM: Artificial Sequence
<220> FEATURE:
<223> OTHER INFORMATION: NCAM (FGL peptide)

<400> SEQUENCE: 34

Glu Val Tyr Val Val Ala Glu Asn Gln Gln Gly Lys Ser Lys Ala
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: FGF system peptide inhibitor
```

```
<400> SEQUENCE: 35

His Phe Lys Asp Pro Lys Arg Leu Tyr
1               5
```

METHODS FOR TREATING DEPRESSION USING NCAM PEPTIDE MIMETICS

CROSS-REFERENCES TO RELATED APPLICATIONS

This application is a continuation of U.S. patent application Ser. No. 12/093,437, filed Apr. 8, 2009, which application is a National Stage application of PCT/US2006/044057, filed Nov. 13, 2006, which application claims the benefit under 35 USC 119(e) of U.S. Provisional Patent Application No. 60/829,516, filed Oct. 13, 2006 and U.S. Provisional Patent Application No. 60/736,526, filed Nov. 12, 2005.

FEDERALLY-SPONSORED RESEARCH OR DEVELOPMENT

This invention was made with Government support under contract MH060398 awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -17-4.TXT, created on Jul. 9, 2012, 16,384 bytes, machine format IBM-PC, MS-Windows operating system, is hereby incorporated by reference in its entirety for all purposes.

BACKGROUND OF THE INVENTION

Clinical depression, including both bipolar disorders and major depression disorders, is a major public health problem, affecting an estimated 9.5% of the adult population of the United States each year. While it has been hypothesized that mental illness, including mood disorders such as major depression ("MDD") and bipolar disorder ("BP") as well as psychotic disorders such as schizophrenia, may have genetic roots, little progress has been made in identifying gene sequences and gene products that play a role in causing these disorders, as is true for many diseases with a complex genetic origin (see, e.g., Burmeister, Bio. Psychiatry 45:522-532 (1999)).

The current lack of biomarkers and the ineffectiveness and reliability of the diagnosis and rates are important issues for the treatment of mental disorders. For example, around 15% of the population suffers from MDD while approximately 1% suffers from BP disorders. Diagnosing bipolar disorder is difficult when, as it sometimes occurs, the patient presents only symptoms of depression to the clinician. At least 10-15% of BP patients are reported to be misdiagnosed as MDD. The consequences of such misdiagnosis include a delay in being introduced to efficacious treatment with mood stabilizers and a delay in seeking or obtaining counseling specific to bipolar disorder. Also treatment with antidepressants alone induces rapid cycling, switching to manic or mixed state, and consequently increases the risk of suicide. Furthermore, in addition to a lack of efficacy, long onset of action and side effects (sexual, sleep, weight gain, etc.), there are recent concerns relating to the undesirable effects of antidepressants on metabolic syndromes, such as diabetes and hypercholesteremia.

Clearly, there is a need for methods of obtaining accurate and objective information about the physiological and/or genetic status of depressed or potentially suicidal patients, particularly as the patient's physiological and/or genetic status relates to the likely response of the patient to a particular treatment regimen.

BRIEF SUMMARY OF THE INVENTION

The present invention provides novel assays for the diagnosis and detection of various mental illnesses. The assays, which include assays for detecting the level of expression of various genes associated with mental disorders, allow the practitioner to obtain a more accurate diagnosis of mental illness in a subject, and allow the practitioner to distinguish between various mental illnesses and associated pathologies. The invention also provides compositions useful for practicing the methods of invention, and for developing further diagnostic methodologies, as well as new therapeutics, to aid in the treatment of mental illness.

In one embodiment, the present invention provides methods of correlating the expression of FGFR2 splice variants with MDD. Because of the relationship between MDD, BP and psychotic disorders such as schizoaffective disorders or psychotic depression, the splice variants described herein are unique to MDD and can be used for differential diagnosis, treatment and prevention of MDD.

In another embodiment, the present invention provides methods for altering the behavioral profiles of rats by injecting the rats with FGF2, an NCAM peptide mimetic, and a peptide inhibitor of FGF receptors. Both FGF2 and the NCAM peptide mimetic have antidepressant-like effects in the forced swim test when injected intracerebroventricularly. The description and examples presented herein show that the presence of a peptide inhibitor reverses the effect. In one embodiment of the invention, ligands that activate FGF receptors are used for their antidepressant effects in the therapeutic treatment of individuals with MDD.

In another embodiment, the invention provides a set of genes associated with suicide in the amygdala and methods for correlating expression of one or more of those genes with suicidal tendencies (Table 1A and Table 1B). In a related embodiment, the invention provides a set of genes associated with suicide, co-morbidity with substance abuse in MDD patients (Table 1C) and methods of detecting one or more of those genes, correlating those genes with suicide risk in appropriate patients, and methods of treating individuals identified as suicidal or likely to become suicidal.

In another embodiment, the invention also provides methods of correlating the differential expression of particular lithium-responsive genes (Table 2A and Table 2B) with bipolar affective disorder.

In yet other embodiment, the invention provides methods for increasing the memory and learning abilities of adult animals by treating early postnatal animals with FGF2. In yet another embodiment, the invention provides methods for treating memory and learning disabilities in animals deficient in active FGF2 by treating early postnatal animals with FGF2.

In another embodiment, the invention provides a method for facilitating the diagnosis of a mood disorder in a subject, comprising the steps of: (i) measuring the level of expression of a gene, wherein the gene is selected from the group consisting of the genes listed in FIG. 5, FIG. 6, FIG. 7, FIG. 8; Table 2B, Table 3, and/or Table 4; (ii) determining whether the gene is dysregulated relative to a control, wherein dysregulation of the gene indicates an increased likelihood that the subject suffers from a mood disorder; and (iii) recording or reporting any finding with respect to the increased likelihood, i.e., reporting whether there is or is not an increased likelihood that the subject suffers from a mood disorder.

In a related embodiment, the mood disorder in question is bipolar disorder, and the gene whose dysregulation is analyzed is selected from the group consisting of the genes listed in FIG. 5, FIG. 7, FIG. 8, Table 2B, and/or Table 4. In another related embodiment, the mood disorder is major depression disorder and the gene is selected from the group consisting of the genes listed in FIG. 6, FIG. 8, Table 1 and/or Table 3.

In yet another related embodiment of the method for facilitating the diagnosis of a mood disorder in a subject, the gene dysregulation, which is detected and measured, occurs in the subject's brain. In yet another related embodiment, the brain tissue in which the dysregulation occurs is selected from the group consisting of the locus coeruleus, the dorsal raphe, the anterior cingulate cortex, the dorsolateral prefrontal cortex, the hippocampus, and the amygdala. In yet another related embodiment, the gene dysregulation is detected in a cell in which the observed gene expression reflects the gene expression observed in the brain, e.g., a lymphocyte cell.

In yet another related embodiment of the method for facilitating the diagnosis of a mood disorder in a subject, the dysregulation of gene expression is assayed by detecting messenger RNA transcribed from the gene or genes of interest. In yet another related embodiment, gene expression is assayed by selectively detecting, directly or indirectly, the protein product of the gene or gene of interest. In yet another related embodiment, detecting messenger RNA transcribed from the gene of interest comprises the steps of (i) contacting said mRNA with a reagent which selectively associates with said messenger RNA; and (ii) detecting the level of said reagent which selectively associates with said mRNA.

In another related embodiment of the method for facilitating the diagnosis of mood disorder in a subject, the measured level of expression of the gene of interest is higher than a level associated with humans without a mood disorder. In yet another related embodiment, the level of expression of the gene is lower than a level associated with humans without a mood disorder, i.e., the gene is downregulated in subjects with a mood disorder.

In another related embodiment of the method for facilitating the diagnosis of mood disorder in a subject, the level of expression of the gene is detected using a microarray assay, and wherein said gene is one of at least two genes on the microarray.

In other embodiment of the method for facilitating the diagnosis of mood disorder in a subject, the gene is selected from Table 1 and the mood disorder is suicidal. In a related embodiment, the subject was previously diagnosed with a mood disorder associated with an increased likelihood of suicidal activity. In yet another related embodiment, the subject was previously diagnosed with a mood disorder selected from the group consisting of major depression, bipolar disorder, and schizophrenia. In yet another related embodiment, the method further comprises prescribing a treatment for the subject which reduces the likelihood of a suicide attempt by the subject.

In other embodiment of the method for facilitating the diagnosis of mood disorder in a subject, the subject has symptoms of both bipolar disorder and major depressive disorder, and the gene of interest is differently expressed in bipolar subjects versus major depression disorder subjects, thereby facilitating a diagnosis of bipolar disorder or major depressive disorder in said subject.

In other embodiment of the method for facilitating the diagnosis of mood disorder in a subject, the gene of interest is dysregulated in substance-abusing MDD subjects versus MDD subjects who are not substance abusers, and the gene of interest is selected from the dysregulated genes listed in Table 1C, thereby facilitating a diagnosis of MDD versus a diagnosis of MDD in addition to substance abuse.

In another embodiment, the invention provides a method of identifying a compound for treatment or prevention of a mood disorder, the method comprising the steps of: (i) contacting the compound with a polypeptide or polynucleotide corresponding to a dysregulated gene selected from the group of dysregulated genes listed in FIG. 5, FIG. 6, FIG. 7, FIG. 8; Table 2B, Table 3, and Table 4; and (ii) determining the functional effect of the compound upon the polypeptide or polynucleotide (e.g., inhibition or enhancement of activity), thereby identifying a compound for treatment or prevention of a mood disorder. In a related embodiment, the contacting step is performed in vitro. In yet another related embodiment, the polypeptide is expressed in a cell and the cell is contacted with the compound. In yet another related embodiment, the mood disorder is selected from the group consisting of bipolar disorder, major depression disorder, suicidal, and substance abuse comorbidity. In yet another related embodiment, the method further comprising administering the identified or candidate compound to an animal and determining the effect on the animal, e.g., determining the effect on the animal's mental health and behavioral phenotype.

In another embodiment, the invention also provides a method of treating a subject who is prone to suicide, comprising the step of administering to the subject a therapeutically effective amount of a polypeptide, the polypeptide encoded by a polynucleotide corresponding to a gene listed in Table 1 or Table 2.

In another embodiment, the invention also provides a method of treating symptoms of anxiety in a subject (e.g., an animal such as a mouse, cat, dog, horse or human), comprising the step of administering a sufficient amount of FGF2 peptide to the subject after the subject has been diagnosed with anxiety or an illness associated with anxiety. In a related embodiment, the subject is a human. In another related embodiment, the sufficient amount of FGF2 is a dose administered at least twice weekly over a period at least one week in length. In yet another related embodiment, the illness being treated is Major Depression or Major Depressive Disorder.

In another embodiment, the invention provides a method for diagnosing a human suffering from chronic stress comprising a) obtaining a nucleic acid sample from the subject; and b) determining the exon IIIb:IIIc splice variant ratio of the expressed gene selected from the group consisting of FGFR2 and FGFR3, wherein a ratio less than approximately 10 is associated with an increased likelihood that said human is suffering from chronic stress. In a related embodiment, the gene is FGFR2. In another related embodiment, the gene is FGFR3. In another related embodiment, the method further comprises administering a pharmacological treatment to a human diagnosed with chronic stress using the method.

In another embodiment, the invention provides a method for identifying a compound which alters the exon IIIb:IIIc splice variant ratio of an expressed gene selected from the group consisting of FGFR2 and FGFR3 in a living animal, comprising a) identifying at least one animal suffering from chronic stress; b) measuring the exon IIIb:IIIc splice variant ratio in said at least one animal; c) administering a test compound to said at least one animal; d) measuring the splice variant ratio a second time after the administration of said test compound; recording the identity of the test compound if said measurement shows that the splice variant ratio is increased.

In another embodiment, the invention provides a method for treating a subject suffering from a glutamatergic imbalance comprising administering to the subject a sufficient amount of a compound which targets a molecule selected from the group consisting of: glial transporters, glutamine synthetase, AMPA, kainate, GRM1 and GRM7.

In yet another embodiment, the invention provides a method for increasing neurite growth in a subject suffering from MDD, comprising administering to the subject a sufficient amount of a compound which targets FGFR3, TrkB receptor, or a growth hormone receptor, or which mimics the actions of FGF2.

In another embodiment, the invention provides a method for detecting global glial alterations in a subject suffering from MDD, comprising the steps of determining the level of gene expression in the LC region of a subject, wherein at least one gene whose level is examined is a glial marker gene selected from the group of glial marker genes in Table 3.

In yet another embodiment, the invention provides a method for distinguishing between BP and MDD in a human subject, comprising a) measuring the level of expression of at least one MDD- or BP-specific gene in DR tissue of said subject, wherein said MDD- or BP-specific gene is selected from the MDD- or BP-specific dysregulated genes listed in Table 4; b) and identifying an increased likelihood that said subject suffers from BP versus MDD, wherein downregulation of an MDD-specific gene in Table 4 correlates with an increased likelihood of MDD in said subject, and wherein downregulation of a BP-specific gene in Table 4 correlates with an increased likelihood of BP in said subject. In a related embodiment, the method further comprises recording or reporting the risk of developing BP or MDD. In a related embodiment, the risk is reported to a physician or to the subject.

In yet another embodiment, the invention provides a method for identifying a human subject with an increased risk of BP or MDD, comprising: (i) measuring the level of expression of a dysregulated gene selected from the genes listed in Table 3; and (ii) correlating said measurement with an increased risk of BP or MDD in said subject. In a related embodiment, the method further comprises recording or reporting the risk of developing BP or MDD. In a related embodiment, the risk is reported to a physician or to the subject.

In yet another embodiment, the invention provides a method for facilitating the diagnosis of major depression disorder in a subject, comprising the steps of: (i) measuring the ratio of expression of FGFR2 exon 5 to FGFR2 exon 11; (ii) determining whether said ratio is lower than a control, wherein a lower ratio indicates an increased likelihood that said subject suffers from major depression disorder; and (iii) recording or reporting any finding with respect to said increased likelihood. In a related embodiment, the expression ratio is the ration in said subject's dorsolateral prefrontal cortex.

In another embodiment, the invention provides a method for facilitating the diagnosis of major depression disorder in a subject, comprising the steps of: (i) measuring the expression of FGFR2 exon 9; (ii) determining whether said expression is lower than a control, wherein a lower level of expression indicates an increased likelihood that said subject suffers from major depression disorder; and (iii) recording or reporting any finding with respect to said increased likelihood. In a related embodiment, the expression is in said subject's dorsolateral prefrontal cortex.

In another embodiment, the invention provides a method for improving memory in an animal, comprising administering FGF2 to said animal. In a related embodiment, the animal is a rodent, cat, dog, horse, primate or human. In yet another related embodiment, administration occurs within 48 hours of the birth of said animal. In another related embodiment, the FGF2 is administered subcutaneously. In yet another related embodiment, the FGF2 is administered at 20 ng/g body weight. In yet another related embodiment, the invention provides a non-human animal, e.g., a rodent, which has been treated with FGF2. In a related embodiment, the animal is an adult animal, previously treated with FGF2, with an improved memory relative to an adult animal which was not previously treated (e.g., treated shortly after birth). In other related embodiments, the expression of NCAM in the FGF2-treated animal is decreased relative to that observed in similar untreated animals. In other related embodiments, the expression of at least one gene selected from the group consisting of GAP-43, Rgs4, trkB, CCK, SST and Vgf is increased in the FGF2-treated animals relative to an untreated animal.

BRIEF DESCRIPTION OF THE DRAWINGS

FIG. 4 shows the effects of injections of a peptide inhibitor on mouse depression and anxiety, as measured by the climbing and forced swim test (top) and the elevated plus maze (EPM) test (bottom), respectively. "Open," "center," and "closed" refer to time spent in the open, center and closed parts of the EPM, respectively.

FIG. 5 shows a table listing genes in the cAMP signalling pathway whose expression is significantly dysregulated in the anterior cingulate cortex (AnCg) from patients with bipolar disorder (BPD).

FIG. 6 shows a table listing genes in cAMP signalling pathways whose expression is significantly dysregulated in the anterior cingulate cortex (AnCg) of patients with major depression disorder (MDD).

FIG. 7 shows a table listing genes in the phosphatidylinositol signalling pathway whose expression is significantly dysregulated in the anterior cingulate cortex (AnCg) of patients with bipolar disorder (BPD).

FIG. 8 shows a table listing genes in the phosphatidylinositol signalling pathway whose expression is significantly dysregulated in the anterior cingulate cortex (AnCg) of patients with major depression disorder (MDD).

FIG. 11, top, shows a schematic of the basic structure of FGFR2 and FGFR3 aligned with the exons amplified and described in the Example. Emphasis is placed on the IIIb/IIIc splice variants in the C-terminus of the third Ig-like domain of both receptors (R2 and R3). Exon sequences for FGFR2 and FGFR3 are in no way identical (see FIG. 11, bottom), but exon nomenclature was synchronized to match each exon number to corresponding regions on both R2 and R3 protein structures. The truncated and cleaved isoforms of the FGF receptors are excluded from the schematic. FIG. 11, bottom, shows sequences of forward and reverse FGFR2 and FGFR3 primers (SEQ ID NOS:1-32) designed for real time RT-PCR quantitative analysis. Primers were optimized and designed for maximum efficiency with differential detection for IIIb/IIIc splice variants for both FGFR2 and FGFR3.

FIG. 12 shows two charts which illustrate the chronic stress-induced decrease in the exon IIIc:IIIb splice variant expression ratio in both FGFR2 (top panel) and FGFR3 (bottom panel). V (vehicle); NS (non-stress); Chronic stress (S); FGF-2 (F).

DEFINITIONS

Figure 1:
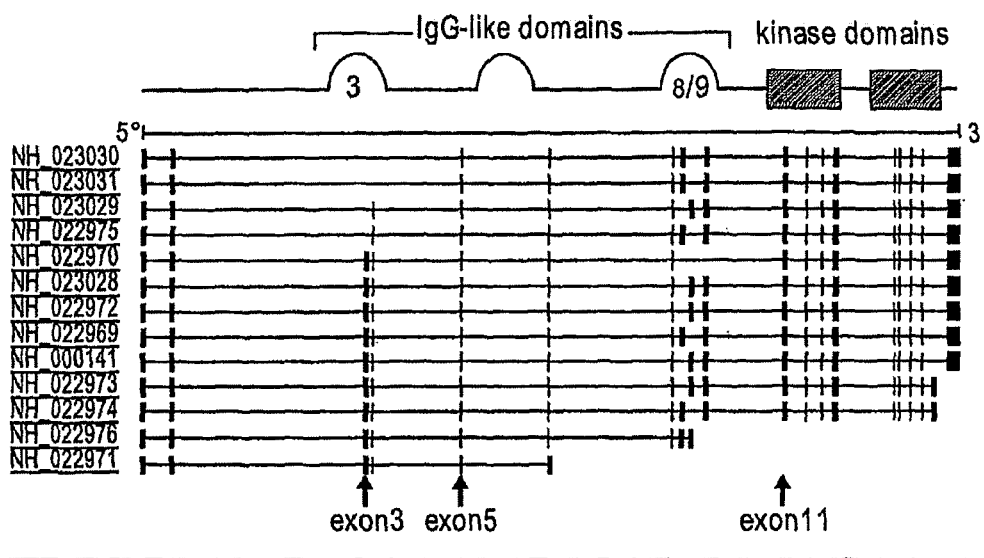
FIG. 1 shows FGFR2 variant differences in Mood Disorders. FGFR2 soluble receptor splice variants may represent a smaller percentage of the total receptors in MDD than in controls.

A "mental disorder" or "mental illness" or "mental disease" or "psychiatric or neuropsychiatric disease or illness or disorder" refers to mood disorders (e.g., major depression, mania, and bipolar disorders), psychotic disorders (e.g., schizophrenia, schizoaffective disorder, schizophreniform disorder, delusional disorder, brief psychotic disorder, and shared psychotic disorder), personality disorders, anxiety disorders (e.g., obsessive-compulsive disorder) as well as other mental disorders such as substance-related disorders, childhood disorders, dementia, autistic disorder, adjustment disorder, delirium, multi-infarct dementia, and Tourette's disorder as described in Diagnostic and Statistical Manual of Mental Disorders, Fourth Edition, (DSM IV). Typically, such disorders have a complex genetic and/or a biochemical component.

A "mood disorder" refers to disruption of feeling tone or emotional state experienced by an individual for an extensive period of time. Mood disorders include major depression disorder (i.e., unipolar disorder), mania, dysphoria, bipolar disorder, dysthymia, cyclothymia and many others. See, e.g., Diagnostic and Statistical Manual of Mental Disorders, Fourth Edition, (DSM IV).

"Major depression disorder," "major depressive disorder," or "unipolar disorder" refers to a mood disorder involving any of the following symptoms: persistent sad, anxious, or "empty" mood; feelings of hopelessness or pessimism; feelings of guilt, worthlessness, or helplessness; loss of interest or pleasure in hobbies and activities that were once enjoyed, including sex; decreased energy, fatigue, being "slowed down"; difficulty concentrating, remembering, or making decisions; insomnia, early-morning awakening, or oversleeping; appetite and/or weight loss or overeating and weight gain; thoughts of death or suicide or suicide attempts; restlessness or irritability; or persistent physical symptoms that do not respond to treatment, such as headaches, digestive disorders, and chronic pain. Various subtypes of depression are described in, e.g., DSM IV.

"Bipolar disorder" is a mood disorder characterized by alternating periods of extreme moods. A person with bipolar disorder experiences cycling of moods that usually swing from being overly elated or irritable (mania) to sad and hopeless (depression) and then back again, with periods of normal mood in between. Diagnosis of bipolar disorder is described in, e.g., DSM IV. Bipolar disorders include bipolar disorder I (mania with or without major depression) and bipolar disorder II (hypomania with major depression), see, e.g., DSM IV.

"A psychotic disorder" refers to a condition that affects the mind, resulting in at least some loss of contact with reality. Symptoms of a psychotic disorder include, e.g., hallucinations, changed behavior that is not based on reality, delusions and the like. See, e.g., DSM IV. Schizophrenia, schizoaffective disorder, schizophreniform disorder, delusional disorder, brief psychotic disorder, substance-induced psychotic disorder, and shared psychotic disorder are examples of psychotic disorders.

"Schizophrenia" refers to a psychotic disorder involving a withdrawal from reality by an individual. Symptoms comprise for at least a part of a month two or more of the following symptoms: delusions (only one symptom is required if a delusion is bizarre, such as being abducted in a space ship from the sun); hallucinations (only one symptom is required if hallucinations are of at least two voices talking to one another or of a voice that keeps up a running commentary on the patient's thoughts or actions); disorganized speech (e.g., frequent derailment or incoherence); grossly disorganized or catatonic behavior; or negative symptoms, i.e., affective flattening, alogia, or avolition. Schizophrenia encompasses disorders such as, e.g., schizoaffective disorders. Diagnosis of schizophrenia is described in, e.g., DSM IV. Types of schizophrenia include, e.g., paranoid, disorganized, catatonic, undifferentiated, and residual.

An "antidepressant" refers to an agents typically used to treat clinical depression. Antidepressants includes compounds of different classes including, for example, specific serotonin reuptake inhibitors (e.g., fluoxetine), tricyclic antidepressants (e.g., desipramine), and dopamine reuptake inhibitors (e.g., bupropion). Typically, antidepressants of different classes exert their therapeutic effects via different biochemical pathways. Often these biochemical pathways overlap or intersect. Additional diseases or disorders often treated with antidepressants include, chronic pain, anxiety disorders, and hot flashes.

An "agonist" refers to an agent that binds to a polypeptide or polynucleotide of the invention, stimulates, increases, activates, facilitates, enhances activation, sensitizes or up regulates the activity or expression of a polypeptide or polynucleotide of the invention.

An "antagonist" refers to an agent that inhibits expression of a polypeptide or polynucleotide of the invention or binds to, partially or totally blocks stimulation, decreases, prevents, delays activation, inactivates, desensitizes, or down regulates the activity of a polypeptide or polynucleotide of the invention.

"Inhibitors," "activators," and "modulators" of expression or of activity are used to refer to inhibitory, activating, or modulating molecules, respectively, identified using in vitro and in vivo assays for expression or activity, e.g., ligands, agonists, antagonists, and their homologs and mimetics. The term "modulator" includes inhibitors and activators. Inhibitors are agents that, e.g., inhibit expression of a polypeptide or polynucleotide of the invention or bind to, partially or totally block stimulation or enzymatic activity, decrease, prevent, delay activation, inactivate, desensitize, or down regulate the activity of a polypeptide or polynucleotide of the invention, e.g., antagonists. Activators are agents that, e.g., induce or activate the expression of a polypeptide or polynucleotide of the invention or bind to, stimulate, increase, open, activate, facilitate, enhance activation or enzymatic activity, sensitize or up regulate the activity of a polypeptide or polynucleotide of the invention, e.g., agonists. Modulators include naturally occurring and synthetic ligands, antagonists, agonists, small chemical molecules and the like. Assays to identify inhibitors and activators include, e.g., applying putative modulator compounds to cells, in the presence or absence of a polypeptide or polynucleotide of the invention and then determining the functional effects on a polypeptide or polynucleotide of the invention activity. Samples or assays comprising a polypeptide or polynucleotide of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a polypeptide or polynucleotide of the invention relative to the control is about 80%, optionally 50% or 25-1%. Activation is achieved when the activity value of a polypeptide or polynucleotide of the invention relative to the control is 110%, optionally 150%, optionally 200-500%, or 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, RNAi, oligonucleotide, etc. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

An "siRNA" or "RNAi" refers to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 or about 24-29 nucleotides in length, e.g., 20, 21, 22, 23, 24, 25, 26, 27, 28, 29, or 30 nucleotides in length.

The term "Table #" when used herein includes all subtables of the Table referred to (e.g., "Table 1" refers to Table 1A, 1B, and Table 1C) unless otherwise indicated.

"Determining the functional effect" refers to assaying for a compound that increases or decreases a parameter that is indirectly or directly under the influence of a polynucleotide or polypeptide of the invention (such as a polynucleotide of FIG. 1, FIGS. 5-8, or Tables 1-4, or a polypeptide encoded by a gene of FIG. 1, FIGS. 5-8, or Tables 1-4), e.g., measuring physical and chemical or phenotypic effects. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the invention or depletion of an substrate; measurement of changes in protein levels of a polypeptide of the invention; measurement of RNA stability; G-protein binding; GPCR phosphorylation or dephosphorylation; signal transduction, e.g., receptor-ligand interactions, second messenger concentrations (e.g., cAMP, IP3, or intracellular $Ca^{2+}$); identification of downstream or reporter gene expression (CAT, luciferase, β-gal, GFP and the like), e.g., via chemiluminescence, fluorescence, colorimetric reactions, antibody binding, inducible markers, and ligand binding assays.

Samples or assays comprising a nucleic acid or protein disclosed herein that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition is achieved when the activity value relative to the control is about 80%, preferably 50%, more preferably 25-0%. Activation is achieved when the activity value relative to the control (untreated with activators) is 110%, more preferably 150%, more preferably 200-500% (i.e., two to five fold higher relative to the control), more preferably 1000-3000% higher.

"Biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Antibody" refers to a polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to V$_H$—C$_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

The terms "peptidomimetic" and "mimetic" refer to a synthetic chemical compound that has substantially the same structural and functional characteristics of the polynucleotides, polypeptides, antagonists or agonists of the invention. Peptide analogs are commonly used in the pharmaceutical industry as non-peptide drugs with properties analogous to those of the template peptide. These types of non-peptide compound are termed "peptide mimetics" or "peptidomimetics" (Fauchere, *Adv. Drug Res.* 15:29 (1986); Veber and Freidinger *TINS* p. 392 (1985); and Evans et al., *J. Med. Chem.* 30:1229 (1987), which are incorporated herein by reference). Peptide mimetics that are structurally similar to therapeutically useful peptides may be used to produce an equivalent or enhanced therapeutic or prophylactic effect. Generally, peptidomimetics are structurally similar to a paradigm polypeptide (i.e., a polypeptide that has a biological or pharmacological activity), such as a CCX CKR, but have one or more peptide linkages optionally replaced by a linkage selected from the group consisting of, e.g., —CH$_2$NH—, —CH$_2$S—, —CH$_2$—CH$_2$—, —CH=CH— (cis and trans), —COCH$_2$—, —CH(OH)CH$_2$—, and —CH$_2$SO—. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. For example, a mimetic composition is within the scope of the invention if it is capable of carrying out the binding or enzymatic activities of a polypeptide or polynucleotide of the invention or inhibiting or increasing the enzymatic activity or expression of a polypeptide or polynucleotide of the invention.

The term "gene" means the segment of DNA involved in producing a polypeptide chain; it includes regions preceding and following the coding region (leader and trailer) as well as intervening sequences (introns) between individual coding segments (exons).

The term "isolated," when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified. In particular, an isolated gene is separated from open reading frames that flank the gene and encode a protein other than the gene of interest. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Cassol et al. (1992); Rossolini et al., *Mol. Cell. Probes* 8:91-98 (1994)). The term nucleic acid is used interchangeably with gene, cDNA, and mRNA encoded by a gene.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine.

Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989)

*Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or 5×SSC, 1% SDS, incubating at 65° C., with wash in 0.2×SSC, and 0.1% SDS at 65° C. Such washes can be performed for 5, 15, 30, 60, 120, or more minutes. Nucleic acids that hybridize to the genes listed in FIG. 1, FIGS. 5-8, or Tables 1-4 are encompassed by the invention. Also encompassed by the invention are arrays comprising nucleotides for detecting the expression of two or more of the genes listed in FIG. 1, FIGS. 5-8, or Tables 1-4.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (1990).

The phrase "a nucleic acid sequence encoding" refers to a nucleic acid that contains sequence information for a structural RNA such as rRNA, a tRNA, or the primary amino acid sequence of a specific protein or peptide, or a binding site for a trans-acting regulatory agent. This phrase specifically encompasses degenerate codons (i.e., different codons which encode a single amino acid) of the native sequence or sequences which may be introduced to conform with codon preference in a specific host cell.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The phrase "specifically (or selectively) binds to an antibody" or "specifically (or selectively) immunoreactive with", when referring to a protein or peptide, refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. For example, antibodies raised against a protein having an amino acid sequence encoded by any of the polynucleotides of the invention can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays, Western blots, or immunohistochemistry are routinely used to select monoclonal antibodies specifically immunoreactive with a protein. See, Harlow and Lane *Antibodies, A Laboratory Manual*, Cold Spring Harbor Publications, NY (1988) for a description of immunoassay formats and conditions that can be used to determine specific immunoreactivity. Typically, a specific or selective reaction will be at least twice the background signal or noise and more typically more than 10 to 100 times background.

One who is "predisposed for a mental disorder" as used herein means a person who has an inclination or a higher likelihood of developing a mental disorder when compared to an average person in the general population.

DETAILED DESCRIPTION OF THE INVENTION

Evidence based on analysis of only a restricted number of molecules suggests altered and unique gene disregulation that may be involved in the pathophysiology of bipolar disorder (BPD) and major depressive disorder (MDD) as well as in the mechanism of drug treatment for these disorders. The recent development of microarray technology allows a comprehensive view of the mRNA expression profiles of specific genes, systems and signaling pathways.

I. Introduction

To understand the genetic basis of mental disorders, studies have been conducted to investigate the expression patterns of genes that are differentially expressed specifically in central nervous system of subjects with mood disorders. In several studies, the differential and unique expression of known and novel genes was determined by way of interrogating total RNA samples purified from postmortem brains of BP and MDD patients with Affymetrix Gene Chips® (containing high-density oligonucleotide probe set arrays). The fundamental principle is that by identifying genes and pathways that are differentially expressed in BP and/or MDD (relative to healthy control subjects), via global expression profiling of the transcriptomes as above, one can identify genes that cause, effect, or are associated with the disease, or that interact with drugs used to treat the disease, for use in diagnostic and therapeutic applications.

The Examples provided herein describe the microarray gene expression profiling of the dorsolateral prefrontal, anterior cingulate, hippocampus, Nucleus Accumbens, Amigdala and cerebellar cortices of BPD and MDD patients. In particular, preferred embodiments of the invention disclosed herein relate to the mRNA expression levels of genes related to the FGF and GPCRs pathways. Other preferred embodiments focus on the detection of splice variants of FGFR2, which are also dysregulated. In still other embodiments, the invention provides genes which are disregulated by lithium for the specific treatment of BP disorders.

The invention also provides nucleic acid sequences and protein sequences which are useful for deciphering the mode of action of currently used mood stabilizers such as lithium. The sequences provided are also useful for drug discovery, e.g., discovering new leads to identifying more efficacious therapeutic targets in the form of a central molecule/pathway through which an entire system or network of pathways can be modulated to remedy the perturbed cellular process underlying MDD, BP, or a principal endophenotype of these disorders. For instance, manipulating GSK3B can affect one or more of the inositol triphosphate, NF-kB family, mitochondrial apoptosis, and ubiquitin-proteasome pathways. Improved knowledge of target-specificity of drugs could help to minimize side effects associated with numerous mood stabilizers currently in use. The invention provides combinations of biomarkers and relevant genes which can be used in methods for diagnosing MDD, BP and related disorders, as well as for developing additional tools for that purpose, and for monitoring drug efficacy.

The present invention provides methods for exploiting the altered expression (either higher or lower expression as indicated herein) or unique differential expression of the genes of FIG. 1, FIGS. 5-8, or Tables 1-4 which is observed in selected brain regions of patients diagnosed with mood disorders (e.g., bipolar disorder and major depression disorder) in comparison with normal individuals. This invention thus provides methods for diagnosis of mental disorders such as mood disorders (e.g., bipolar disorder, major depression, and the like) and other mental disorders having a genetic component by detecting the level of a transcript or translation product of the genes listed in FIG. 1, FIGS. 5-8, or Tables 1-4, as well as their corresponding biochemical pathways.

The invention further provides methods of identifying a compound useful for the treatment of such disorders by selecting compounds, e.g., FGF2, NCAM and peptide inhibitors of the FGF system, that modulate the functional effect of the translation products or the expression of the transcripts described herein. The invention also provides for methods of treating patients with such mental disorders, e.g., by administering the compounds of the invention or by gene therapy.

The invention also provides much-needed tools for researching mental illness and the underlying molecular causes of mental illness. These tools include animal models which have been engineered to exhibit phenotypes which are useful for elucidating the molecular basis for mental abnormalities and for identifying treatments for mental abnormalities. For example, the invention provides in one embodiment a mouse with improved memory and learning ability.

The genes and the polypeptides that they encode, which are associated with mood disorders such as bipolar disease and major depression, are useful for facilitating the design and development of various molecular diagnostic tools such as GeneChips™ containing probe sets specific for all or selected mental disorders, including but not limited to mood disorders, and as an ante- and/or post-natal diagnostic tool for screening newborns in concert with genetic counseling. Other diagnostic applications include evaluation of disease susceptibility, prognosis, and monitoring of disease or treatment process, as well as providing individualized medicine via predictive drug profiling systems, e.g., by correlating specific genomic motifs with the clinical response of a patient to individual drugs. In addition, the present invention is useful for multiplex SNP and haplotype profiling, including but not limited to the identification of therapeutic, diagnostic, and pharmacogenetic targets at the gene, mRNA, protein, and pathway level. Profiling of splice variants and deletions is also useful for diagnostic and therapeutic applications.

The genes and the polypeptides that they encode, described herein, are also useful as drug targets for the development of therapeutic drugs for the treatment or prevention of mental disorders, including but not limited to mood disorders.

Antidepressants belong to different classes, e.g., desipramine, bupropion, and fluoxetine are in general equally effective for the treatment of clinical depression, but act by different mechanisms. The similar effectiveness of the drugs for treatment of mood disorders suggests that they act through a presently unidentified common pathway. Animal models of depression, including treatment of animals with known therapeutics such as SSRIs, can be used to examine the mode of action of the genes of the invention. Lithium is drug of choice for treating BP.

The genes and the polypeptides that they encode, described herein, as also useful as drug targets for the development of therapeutic drugs for the treatment or prevention of mental disorders, including but not limited to mood disorders. Mental disorders have a high co-morbidity with other neurological disorders, such as Parkinson's disease or Alzheimer's. Therefore, the present invention can be used for diagnosis and treatment of patients with multiple disease states that include a mental disorder such as a mood disorder. These mood disorders include BP, MDD, and other disorders such as psychotic-depression, depression and anxiety features, melancholic depression, chronic depression, BPI and BPII.

II. General Recombinant Nucleic Acid Methods for Use with the Invention

In numerous embodiments of the present invention, polynucleotides of the invention will be isolated and cloned using recombinant methods. Such polynucleotides include, e.g., those listed in FIG. 1, FIGS. 5-8, or Tables 1-4, which can be used for, e.g., protein expression or during the generation of variants, derivatives, expression cassettes, to monitor gene expression, for the isolation or detection of sequences of the invention in different species, for diagnostic purposes in a patient, e.g., to detect mutations or to detect expression levels of nucleic acids or polypeptides of the invention. In some embodiments, the sequences of the invention are operably linked to a heterologous promoter. In one embodiment, the nucleic acids of the invention are from any mammal, including, in particular, e.g., a human, a mouse, a rat, a primate, etc.

A. General Recombinant Nucleic Acids Methods

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Desired Proteins In general, the nucleic acids encoding the subject proteins are cloned from DNA sequence libraries that are made to encode cDNA or genomic DNA. The particular sequences can be located by hybridizing with an oligonucleotide probe, the sequence of which can be derived from the sequences of the genes listed in FIG. 1, FIGS. 5-8, or Tables 1-4, which provide a reference for PCR primers and defines suitable regions for isolating specific probes. Alternatively, where the sequence is cloned into an expression library, the expressed recombinant protein can be detected immunologically with antisera or purified antibodies made against a polypeptide comprising an amino acid sequence encoded by a gene listed in FIG. 1, FIGS. 5-8, or Tables 1-4.

Methods for making and screening genomic and cDNA libraries are well known to those of skill in the art (see, e.g., Gubler and Hoffman *Gene* 25:263-269 (1983); Benton and Davis *Science,* 196:180-182 (1977); and Sambrook, supra). Brain cells are an example of suitable cells to isolate RNA and cDNA sequences of the invention.

Briefly, to make the cDNA library, one should choose a source that is rich in mRNA. The mRNA can then be made into cDNA, ligated into a recombinant vector, and transfected into a recombinant host for propagation, screening and cloning. For a genomic library, the DNA is extracted from a suitable tissue and either mechanically sheared or enzymatically digested to yield fragments of preferably about 5-100 kb. The fragments are then separated by gradient centrifugation from undesired sizes and are constructed in bacteriophage lambda vectors. These vectors and phage are packaged in vitro, and the recombinant phages are analyzed by plaque hybridization. Colony hybridization is carried out as generally described in Grunstein et al., *Proc. Natl. Acad. Sci. USA.,* 72:3961-3965 (1975).

An alternative method combines the use of synthetic oligonucleotide primers with polymerase extension on an mRNA or DNA template. Suitable primers can be designed from specific sequences of the invention. This polymerase chain reaction (PCR) method amplifies the nucleic acids encoding the protein of interest directly from mRNA, cDNA, genomic libraries or cDNA libraries. Restriction endonuclease sites can be incorporated into the primers. Polymerase chain reaction or other in vitro amplification methods may also be useful, for example, to clone nucleic acids encoding specific proteins and express said proteins, to synthesize nucleic acids that will be used as probes for detecting the presence of mRNA encoding, a polypeptide of the invention in physiological samples, for nucleic acid sequencing, or for other purposes (see, U.S. Pat. Nos. 4,683,195 and 4,683,202). Genes amplified by a PCR reaction can be purified from agarose gels and cloned into an appropriate vector.

Appropriate primers and probes for identifying polynucleotides of the invention from mammalian tissues can be derived from the sequences provided herein. For a general overview of PCR, see, Innis et al. *PCR Protocols: A Guide to Methods and Applications*, Academic Press, San Diego (1990).

Synthetic oligonucleotides can be used to construct genes. This is done using a series of overlapping oligonucleotides, usually 40-120 bp in length, representing both the sense and anti-sense strands of the gene. These DNA fragments are then annealed, ligated and cloned.

A gene encoding a polypeptide of the invention can be cloned using intermediate vectors before transformation into mammalian cells for expression. These intermediate vectors are typically prokaryote vectors or shuttle vectors. The proteins can be expressed in either prokaryotes, using standard methods well known to those of skill in the art, or eukaryotes as described infra.

III. Purification of Proteins of the Invention

Either naturally occurring or recombinant polypeptides of the invention can be purified for use in functional assays. Naturally occurring polypeptides, e.g., polypeptides encoded by genes listed in FIG. 1, FIGS. 5-8, or Tables 1-4, can be purified, for example, from mouse or human tissue such as brain or any other source of an ortholog. Recombinant polypeptides can be purified from any suitable expression system.

The polypeptides of the invention may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant polypeptides are purified. For example, proteins having established molecular adhesion properties can be reversible fused to polypeptides of the invention. With the appropriate ligand, the polypeptides can be selectively adsorbed to a purification column and then freed from the column in a relatively pure form. The fused, protein is then removed by enzymatic activity. Finally the polypeptide can be purified using immunoaffinity columns.

A. Purification of Proteins from Recombinant Bacteria

When recombinant proteins are expressed by the transformed bacteria in large amounts, typically after promoter induction, although expression can be constitutive, the proteins may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells typically, but not limited to, by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook et al., both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques.

Alternatively, it is possible to purify proteins from bacteria periplasm. Where the protein is exported into the periplasm of the bacteria, the periplasmic fraction of the bacteria can be isolated by cold osmotic shock in addition to other methods known to those of skill in the art (see, Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

1. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

2. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The proteins of interest can also be separated from other proteins on the basis of their size, net surface charge, hydrophobicity and affinity for ligands. In addition, antibodies raised against proteins can be conjugated to column matrices and the proteins immunopurified. All of these methods are well known in the art.

It will be apparent to one of skill that chromatographic techniques can be performed at any scale and using equipment from many different manufacturers (e.g., Pharmacia Biotech).

IV. Detection of Gene Expression

Those of skill in the art will recognize that detection of expression of polynucleotides of the invention has many uses. For example, as discussed herein, detection of the level of polypeptides or polynucleotides of the invention in a patient is useful for diagnosing mood disorders or psychotic disorders or a predisposition for a mood disorder or psychotic disorders. Moreover, detection of gene expression is useful to identify modulators of expression of the polypeptides or polynucleotides of the invention.

A variety of methods of specific DNA and RNA measurement using nucleic acid hybridization techniques are known to those of skill in the art (see, Sambrook, supra). Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention.

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins *Nucleic Acid Hybridization, A Practical Approach*, IRL Press (1985); Gall and Pardue, *Proc. Natl. Acad. Sci. U.S.A.*, 63:378-383 (1969); and John et al. *Nature*, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "*Practice and Theory of Enzyme Immunoassays*," *Laboratory Techniques in Biochemistry and Molecular Biology*, Burdon and van Knippenberg Eds., Elsevier (1985), pp. 9-20).

The probes are typically labeled either directly, as with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labeled probes or the like.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden *Introduction to Immunocytochemistry*, 2nd ed., Springer Verlag, NY (1997); and in Haugland *Handbook of Fluorescent Probes and Research Chemicals*, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) *Science*, 251: 767-777; Sheldon et al. (1993) *Clinical Chemistry* 39(4): 718-719, and Kozal et al. (1996) *Nature Medicine* 2(7): 753-759.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) *Analytical Biochemistry* 181:153-162; Bogulayski (1986) et al. *J. Immunol. Methods* 89:123-130; Prooijen-Knegt (1982) *Exp. Cell Res.* 141:397-407;

Rudkin (1976) *Nature* 265:472-473, Stollar (1970) *Proc. Nat'l Acad. Sci. USA* 65:993-1000; Ballard (1982) *Mol. Immunol.* 19:793-799; Pisetsky and Caster (1982) *Mol. Immunol.* 19:645-650; Viscidi et al. (1988) *J. Clin. Microbial.* 41:199-209; and Kiney et al. (1989) *J. Clin. Microbiol.* 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) *Fundamental Immunology* Raven Press, Ltd., NY (1993); Coligan *Current Protocols in Immunology* Wiley/Greene, NY (1991); Harlow and Lane *Antibodies: A Laboratory Manual* Cold Spring Harbor Press, NY (1988); Stites et al. (eds.) *Basic and Clinical Immunology* (4th ed.) Lange Medical Publications, Los Altos, Calif., and references cited therein; Goding *Monoclonal Antibodies: Principles and Practice* (2d ed.) Academic Press, New York, N.Y., (1986); and Kohler and Milstein *Nature* 256: 495-497 (1975)). Other suitable techniques for antibody preparation include selection of libraries of recombinant antibodies in phage or similar vectors (see, Huse et al. *Science* 246:1275-1281 (1989); and Ward et al. *Nature* 341:544-546 (1989)). Specific monoclonal and polyclonal antibodies and antisera will usually bind with a $K_D$ of at least about 0.1 μM, preferably at least about 0.01 μM or better, and most typically and preferably, 0.001 μM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation.

An alternative means for determining the level of expression of the nucleic acids of the present invention is in situ hybridization. In situ hybridization assays are well known and are generally described in Angerer et al., *Methods Enzymol.* 152:649-660 (1987). In an in situ hybridization assay, cells, preferentially human cells from the cerebellum or the hippocampus, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

V. Immunological Detection of the Polypeptides of the Invention

In addition to the detection of polynucleotide expression using nucleic acid hybridization technology, one can also use immunoassays to detect polypeptides of the invention. Immunoassays can be used to qualitatively or quantitatively analyze polypeptides. A general overview of the applicable technology can be found in Harlow & Lane, *Antibodies: A Laboratory Manual* (1988).

A. Antibodies to Target Polypeptides or Other Immunogens

Methods for producing polyclonal and monoclonal antibodies that react specifically with a protein of interest or other immunogen are known to those of skill in the art (see, e.g., Coligan, supra; and Harlow and Lane, supra; Stites et al., supra and references cited therein; Goding, supra; and Kohler and Milstein *Nature,* 256:495-497 (1975)). Such techniques include antibody preparation by selection of antibodies from libraries of recombinant antibodies in phage or similar vectors (see, Huse et al., supra; and Ward et al., supra). For example, in order to produce antisera for use in an immunoassay, the protein of interest or an antigenic fragment thereof, is isolated as described herein. For example, a recombinant protein is produced in a transformed cell line. An inbred strain of mice or rabbits is immunized with the protein using a standard adjuvant, such as Freund's adjuvant, and a standard immunization protocol. Alternatively, a synthetic peptide derived from the sequences disclosed herein and conjugated to a carrier protein can be used as an immunogen.

Polyclonal sera are collected and titered against the immunogen in an immunoassay, for example, a solid phase immunoassay with the immunogen immobilized on a solid support. Polyclonal antisera with a titer of $10^4$ or greater are selected and tested for their cross-reactivity against unrelated proteins or even other homologous proteins from other organisms, using a competitive binding immunoassay. Specific monoclonal and polyclonal antibodies and antisera will usually bind with a $K_D$ of at least about 0.1 mM, more usually at least about 1 μM, preferably at least about 0.1 μM or better, and most preferably, 0.01 μM or better.

A number of proteins of the invention comprising immunogens may be used to produce antibodies specifically or selectively reactive with the proteins of interest. Recombinant protein is the preferred immunogen for the production of monoclonal or polyclonal antibodies. Naturally occurring protein, such as one comprising an amino acid sequence encoded by a gene listed in Tables 1-4 and FIG. 1 may also be used either in pure or impure form. Synthetic peptides made using the protein sequences described herein may also be used as an immunogen for the production of antibodies to the protein. Recombinant protein can be expressed in eukaryotic or prokaryotic cells and purified as generally described supra. The product is then injected into an animal capable of producing antibodies. Either monoclonal or polyclonal antibodies may be generated for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the protein can be done if desired (see, Harlow and Lane, supra).

Monoclonal antibodies may be obtained using various techniques familiar to those of skill in the art. Typically, spleen cells from an animal immunized with a desired antigen are immortalized, commonly by fusion with a myeloma cell (see, Kohler and Milstein, *Eur. J. Immunol.* 6:511-519 (1976)). Alternative methods of immortalization include, e.g., transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., supra.

Once target protein specific antibodies are available, the protein can be measured by a variety of immunoassay methods with qualitative and quantitative results available to the clinician. For a review of immunological and immunoassay procedures in general see, Stites, supra. Moreover, the immunoassays of the present invention can be performed in any of several configurations, which are reviewed extensively in Maggio *Enzyme Immunoassay*, CRC Press, Boca Raton, Fla. (1980); Tijssen, supra; and Harlow and Lane, supra.

Immunoassays to measure target proteins in a human sample may use a polyclonal antiserum that was raised to the protein (e.g., one has an amino acid sequence encoded by a gene listed FIG. 1, FIGS. 5-8, or Tables 1-4) or a fragment thereof. This antiserum is selected to have low cross-reactivity against different proteins and any such cross-reactivity is removed by immunoabsorption prior to use in the immunoassay.

B. Immunological Binding Assays

In a preferred embodiment, a protein of interest is detected and/or quantified using any of a number of well-known immunological binding assays (see, e.g., U.S. Pat. Nos. 4,366,241; 4,376,110; 4,517,288; and 4,837,168). For a review of the general immunoassays, see also Asai *Methods in Cell Biology Volume* 37: *Antibodies in Cell Biology*, Academic Press, Inc. NY (1993); Stites, supra. Immunological binding assays (or immunoassays) typically utilize a "capture agent" to specifically bind to and often immobilize the analyte (in this case a polypeptide of the present invention or antigenic subsequences thereof). The capture agent is a moiety that specifically binds to the analyte. In a preferred embodiment, the capture agent is an antibody that specifically binds, for example, a polypeptide of the invention. The antibody may be produced by any of a number of means well known to those of skill in the art and as described above.

Immunoassays also often utilize a labeling agent to specifically bind to and label the binding complex formed by the capture agent and the analyte. The labeling agent may itself be one of the moieties comprising the antibody/analyte complex. Alternatively, the labeling agent may be a third moiety, such as another antibody, that specifically binds to the antibody/protein complex.

In a preferred embodiment, the labeling agent is a second antibody bearing a label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111:1401-1406 (1973); and Akerstrom, et al. *J. Immunol.*, 135:2589-2542 (1985)).

Throughout the assays, incubation and/or washing steps may be required after each combination of reagents. Incubation steps can vary from about 5 seconds to several hours, preferably from about 5 minutes to about 24 hours. The incubation time will depend upon the assay format, analyte, volume of solution, concentrations, and the like. Usually, the assays will be carried out at ambient temperature, although they can be conducted over a range of temperatures, such as 10° C. to 40° C.

1. Non-Competitive Assay Formats

Immunoassays for detecting proteins of interest from tissue samples may be either competitive or noncompetitive. Noncompetitive immunoassays are assays in which the amount of captured analyte (in this case the protein) is directly measured. In one preferred "sandwich" assay, for example, the capture agent (e.g., antibodies specific for a polypeptide encoded by a gene listed in FIG. 1, FIGS. 5-8, or Tables 1-4) can be bound directly to a solid substrate where it is immobilized. These immobilized antibodies then capture the polypeptide present in the test sample. The polypeptide thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats

In competitive assays, the amount of analyte (such as a polypeptide encoded by a gene listed in FIG. 1, FIGS. 5-8, or Tables 1-4) present in the sample is measured indirectly by measuring the amount of an added (exogenous) analyte displaced (or competed away) from a capture agent (e.g., an antibody specific for the analyte) by the analyte present in the sample. In one competitive assay, a known amount of, in this case, the protein of interest is added to the sample and the sample is then contacted with a capture agent, in this case an antibody that specifically binds to a polypeptide of the invention. The amount of immunogen bound to the antibody is inversely proportional to the concentration of immunogen present in the sample. In a particularly preferred embodiment, the antibody is immobilized on a solid substrate. For example, the amount of the polypeptide bound to the antibody may be determined either by measuring the amount of subject protein present in a protein/antibody complex or, alternatively, by measuring the amount of remaining uncomplexed protein. The amount of protein may be detected by providing a labeled protein molecule.

Immunoassays in the competitive binding format can be used for cross-reactivity determinations. For example, a protein of interest can be immobilized on a solid support. Proteins are added to the assay which compete with the binding of the antisera to the immobilized antigen. The ability of the above proteins to compete with the binding of the antisera to the immobilized protein is compared to that of the protein of interest. The percent cross-reactivity for the above proteins is calculated, using standard calculations. Those antisera with less than 10% cross-reactivity with each of the proteins listed above are selected and pooled. The cross-reacting antibodies are optionally removed from the pooled antisera by immunoabsorption with the considered proteins, e.g., distantly related homologs.

The immunoabsorbed and pooled antisera are then used in a competitive binding immunoassay as described above to compare a second protein, thought to be perhaps a protein of the present invention, to the immunogen protein. In order to make this comparison, the two proteins are each assayed at a wide range of concentrations and the amount of each protein required to inhibit 50% of the binding of the antisera to the immobilized protein is determined. If the amount of the second protein required is less than 10 times the amount of the protein partially encoded by a sequence herein that is required, then the second protein is said to specifically bind to an antibody generated to an immunogen consisting of the target protein.

3. Other Assay Formats

In a particularly preferred embodiment, western blot (immunoblot) analysis is used to detect and quantify the presence of a polypeptide of the invention in the sample. The technique generally comprises separating sample proteins by gel electrophoresis on the basis of molecular weight, transferring the separated proteins to a suitable solid support (such as, e.g., a nitrocellulose filter, a nylon filter, or a derivatized nylon filter) and incubating the sample with the antibodies that specifically bind the protein of interest. For example, the antibodies specifically bind to a polypeptide of interest on the solid support. These antibodies may be directly labeled or alternatively may be subsequently detected using labeled antibodies (e.g., labeled sheep anti-mouse antibodies) that specifically bind to the antibodies against the protein of interest.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

4. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical or chemical means. Useful labels in the present invention include magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, the ease of conjugation with the compound, stability requirements, available instrumentation, and disposal provisions.

Non-radioactive labels are often attached by indirect means. The molecules can also be conjugated directly to signal generating compounds, e.g., by conjugation with an enzyme or fluorescent compound. A variety of enzymes and fluorescent compounds can be used with the methods of the present invention and are well-known to those of skill in the art (for a review of various labeling or signal producing systems which may be used, see, e.g., U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected directly by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need to be labeled and the presence of the target antibody is detected by simple visual inspection.

In some embodiments, BP or MDD in a patient may be diagnosed or otherwise evaluated by visualizing expression in situ of one or more of the appropriately dysregulated gene sequences identified herein, e.g., FIG. 1, FIGS. 5-8, or Tables 1-4. Those skilled in the art of visualizing the presence or expression of molecules including nucleic acids, polypeptides and other biochemicals in the brains of living patients will appreciate that the gene expression information described herein may be utilized in the context of a variety of visualization methods. Such methods include, but are not limited to, single-photon emission-computed tomography (SPECT) and positron-emitting tomography (PET) methods. See, e.g., Vassaux and Groot-wassink, "In Vivo Noninvasive Imaging for Gene Therapy," J. Biomedicine and Biotechnology, 2: 92-101 (2003).

PET and SPECT imaging shows the chemical functioning of organs and tissues, while other imaging techniques—such as X-ray, CT and MRI—show structure. The use of PET and SPECT imaging is useful for qualifying and monitoring the development of brain diseases, including bipolar disorder, major depression disorder, schizophrenia and associated disorders. In some instances, the use of PET or SPECT imaging allows diseases to be detected years earlier than the onset of symptoms. The use of small molecules for labelling and visualizing the presence or expression of polypeptides and nucleotides has had success, for example, in visualizing proteins in the brains of Alzheimer's patients, as described by, e.g., Herholz K et al., Mol Imaging Biol., 6(4):239-69 (2004); Nordberg A, Lancet Neurol., 3(9):519-27 (2004); Neuropsychol Rev., Zakzanis K K et al., 13(1):1-18 (2003); Kung M P et al, Brain Res., 1025(1-2):98-105 (2004); and Herholz K, Ann Nucl Med., 17(2):79-89 (2003).

The dysregulated genes disclosed in FIG. 1, FIGS. 5-8, or Tables 1-4, or their encoded peptides (if any), or fragments thereof, can be used in the context of PET and SPECT imaging applications. After modification with appropriate tracer residues for PET or SPECT applications, molecules which interact or bind with the transcripts in Tables FIG. 1, FIGS. 5-8, or Tables 1-4 or with any polypeptides encoded by those transcripts may be used to visualize the patterns of gene expression and facilitate diagnosis of schizophrenia, MDD, BP, and related disorders as described herein. Similarly, if the encoded polypeptides encode enzymes, labeled molecules which interact with the products of catalysis by the enzyme may be used for the in vivo imaging and diagnostic application described herein.

Antisense technology is particularly suitable for detecting the transcripts identified in FIG. 1, FIGS. 5-8, or Tables 1-4. For example, the use of antisense peptide nucleic acid (PNA) labeled with an appropriate radionuclide, such as $^{111}$In, and conjugated to a brain drug-targeting system to enable transport across biologic membrane barriers, has been demonstrated to allow imaging of endogenous gene expression in brain cancer. See Suzuki et al., Journal of Nuclear Medicine, 10:1766-1775 (2004). Suzuki et al. utilize a delivery system comprising monoclonal antibodies that target transferring receptors at the blood-brain barrier and facilitate transport of the PNA across that barrier. Modified embodiments of this technique may be used to target upregulated genes associated with schizophrenia, BP or MDD, such as the upregulated genes which appear in FIG. 1, FIGS. 5-8, or Tables 1-4, in methods of treating schizophrenic, BP or MDD patients.

In other embodiments, the dysregulated genes listed in FIG. 1, FIGS. 5-8, or Tables 1-4 may be used in the context of prenatal and neonatal diagnostic methods. For example, fetal or neonatal samples can be obtained and the expression levels of appropriate transcripts (e.g., the transcripts in FIG. 1, FIGS. 5-8, or Tables 1-4) may be measured and correlated with the presence or increased likelihood of a mental disorder, e.g., MDD. Similarly, the presence of one or more of the SNPs identified in FIG. 1 may be used to infer or corroborate dysregulated expression of a gene and the likelihood of a mood disorder in prenatal, neonatal, children and adult patients.

In other embodiments, the brain labeling and imaging techniques described herein or variants thereof may be used in conjunction with any of the dysregulated gene sequences in FIG. 1, FIGS. 5-8, or Tables 1-4 in a forensic analysis, i.e., to determine whether a deceased individual suffered from schizophrenia, BP, or MDD.

VI. Screening for Modulators of Polypeptides and Polynucleotides of the Invention Modulators of polypeptides or polynucleotides of the invention, i.e. agonists or antagonists of their activity or modulators of polypeptide or polynucleotide expression, are useful for treating a number of human diseases, including mood disorders or psychotic disorders. Administration of agonists, antagonists or other agents that modulate expression of the polynucleotides, or polypeptides of the invention can be used to treat patients with mood disorders or psychotic disorders.

A. Screening Methods

A number of different screening protocols can be utilized to identify agents that modulate the level of expression or activity of polypeptides and polynucleotides of the invention in cells, particularly mammalian cells, and especially human cells. In general terms, the screening methods involve screening a plurality of agents to identify an agent that modulates the polypeptide activity by binding to a polypeptide of the invention, modulating inhibitor binding to the polypeptide or activating expression of the polypeptide or polynucleotide, for example.

1. Binding Assays

Preliminary screens can be conducted by screening for agents capable of binding to a polypeptide of the invention, as at least some of the agents so identified are likely modulators of polypeptide activity. The binding assays usually involve contacting a polypeptide of the invention with one or more test agents and allowing sufficient time for the protein and test agents to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots (see, e.g., Bennet and Yamamura, (1985) "Neurotransmitter, Hormone or Drug Receptor Binding Methods," in *Neurotransmitter Receptor* Binding (Yamamura, H. I., et al., eds.), pp. 61-89. The protein utilized in such assays can be naturally expressed, cloned or synthesized.

Binding assays are also useful, e.g., for identifying endogenous proteins that interact with a polypeptide of the invention. For example, antibodies, receptors or other molecules that bind a polypeptide of the invention can be identified in binding assays.

2. Expression Assays

Certain screening methods involve screening for a compound that up or down-regulates the expression of a polypeptide or polynucleotide of the invention. Such methods generally involve conducting cell-based assays in which test compounds are contacted with one or more cells expressing a polypeptide or polynucleotide of the invention and then detecting an increase or decrease in expression (either transcript, translation product, or catalytic product). Some assays are performed with peripheral cells, or other cells, that express an endogenous polypeptide or polynucleotide of the invention.

Polypeptide or polynucleotide expression can be detected in a number of different ways. As described infra, the expression level of a polynucleotide of the invention in a cell can be determined by probing the mRNA expressed in a cell with a probe that specifically hybridizes with a transcript (or complementary nucleic acid derived therefrom) of a polynucleotide of the invention. Probing can be conducted by lysing the cells and conducting Northern blots or without lysing the cells using in situ-hybridization techniques. Alternatively, a polypeptide of the invention can be detected using immunological methods in which a cell lysate is probed with antibodies that specifically bind to a polypeptide of the invention.

Other cell-based assays are reporter assays conducted with cells that do not express a polypeptide or polynucleotide of the invention. Certain of these assays are conducted with a heterologous nucleic acid construct that includes a promoter of a polynucleotide of the invention that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, β-glucuronidase, chloramphenicol acetyl transferase (CAT); Alton and Vapnek (1979) *Nature* 282:864-869), luciferase, β-galactosidase, green fluorescent protein (GFP) and alkaline phosphatase (Toh, et al. (1980) *Eur. J. Biochem.* 182:231-238; and Hall et al. (1983) *J. Mol. Appl. Gen.* 2:101).

In these assays, cells harboring the reporter construct are contacted with a test compound. A test compound that either activates the promoter by binding to it or triggers a cascade that produces a molecule that activates the promoter causes expression of the detectable reporter. Certain other reporter assays are conducted with cells that harbor a heterologous construct that includes a transcriptional control element that activates expression of a polynucleotide of the invention and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

The level of expression or activity can be compared to a baseline value. As indicated above, the baseline value can be a value for a control sample or a statistical value that is representative of expression levels for a control population (e.g., healthy individuals not having or at risk for mood disorders or psychotic disorders). Expression levels can also be determined for cells that do not express a polynucleotide of the invention as a negative control. Such cells generally are otherwise substantially genetically the same as the test cells.

A variety of different types of cells can be utilized in the reporter assays. Cells that express an endogenous polypeptide or polynucleotide of the invention include, e.g., brain cells, including cells from the cerebellum, anterior cingulate cortex, dorsolateral prefrontal cortex, amygdala, hippocampus, or nucleus accumbens. Cells that do not endogenously express polynucleotides of the invention can be prokaryotic, but are preferably eukaryotic. The eukaryotic cells can be any of the cells typically utilized in generating cells that harbor recombinant nucleic acid constructs. Exemplary eukaryotic cells include, but are not limited to, yeast, and various higher eukaryotic cells such as the COS, CHO and HeLa cell lines.

Various controls can be conducted to ensure that an observed activity is authentic including running parallel reactions with cells that lack the reporter construct or by not contacting a cell harboring the reporter construct with test compound. Compounds can also be further validated as described below.

3. Catalytic Activity

Catalytic activity of polypeptides of the invention can be determined by measuring the production of enzymatic products or by measuring the consumption of substrates. Activity refers to either the rate of catalysis or the ability to the polypeptide to bind ($K_m$) the substrate or release the catalytic product ($K_d$).

Analysis of the activity of polypeptides of the invention are performed according to general biochemical analyses. Such assays include cell-based assays as well as in vitro assays involving purified or partially purified polypeptides or crude cell lysates. The assays generally involve providing a known quantity of substrate and quantifying product as a function of time.

4. Validation

Agents that are initially identified by any of the foregoing screening methods can be further tested to validate the apparent activity. Preferably such studies are conducted with suitable animal models. The basic format of such methods involves administering a lead compound identified during an initial screen to an animal that serves as a model for humans and then determining if expression or activity of a polynucleotide or polypeptide of the invention is in fact upregulated. The animal models utilized in validation studies generally are mammals of any kind. Specific examples of suitable animals include, but are not limited to, primates, mice, and rats. As described herein, models using administration of known therapeutics can be useful.

5. Animal Models

Animal models of mental disorders also find use in screening for modulators. In one embodiment, invertebrate models such as Drosophila models can be used, screening for modulators of Drosophila orthologs of the human genes disclosed herein. In another embodiment, transgenic animal technology including gene knockout technology, for example as a result of homologous recombination with an appropriate gene targeting vector, or gene overexpression, will result in the absence, decreased or increased expression of a polynucleotide or polypeptide of the invention. The same technology can also be applied to make knockout cells. When desired, tissue-specific expression or knockout of a polynucleotide or polypeptide of the invention may be necessary. Transgenic animals generated by such methods find use as animal models of mental illness and are useful in screening for modulators of mental illness.

Knockout cells and transgenic mice can be made by insertion of a marker gene or other heterologous gene into an endogenous gene site in the mouse genome via homologous recombination. Such mice can also be made by substituting an endogenous polynucleotide of the invention with a mutated version of the polynucleotide, or by mutating an endogenous polynucleotide, e.g., by exposure to carcinogens.

For development of appropriate stem cells, a DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244: 1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators of Polypeptides or Polynucleotides of the Invention

The agents tested as modulators of the polypeptides or polynucleotides of the invention can be any small chemical compound, or a biological entity, such as a protein, sugar, nucleic acid or lipid. Alternatively, modulators can be genetically altered versions of a polypeptide or polynucleotides, e.g., recombinant or altered versions of FGF2, NCAM, or a peptide inhibitor of the FGF system. Typically, test compounds will be small chemical molecules and peptides. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like. Modulators also include agents designed to reduce the level of mRNA of the invention (e.g. antisense molecules, ribozymes, DNAzymes and the like) or the level of translation from an mRNA.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569, 588; thiazolidinones and metathiazanones, U.S. Pat. No. 5,549,974; pyrrolidines, U.S. Pat. Nos. 5,525,735 and 5,519, 134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, numerous combinatorial libraries are themselves commercially available (see, e.g., ComGenex, Princeton, N.J.; Tripos; Inc., St. Louis, Mo.; 3D Pharmaceuticals, Exton, Pa.; Martek Biosciences, Columbia, Md., etc.).

C. Solid State and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds are possible using the integrated systems of the invention. More recently, microfluidic approaches to reagent manipulation have been developed.

The molecule of interest can be bound to the solid state component, directly or indirectly, via covalent or non-covalent linkage, e.g., via a tag. The tag can be any of a variety of components. In general, a molecule that binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders (see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs, such as agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g., which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:33). Such flexible linkers are known to those of skill in the art. For example, poly(ethylene glycol) linkers are available from Shearwater Polymers, Inc., Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature (see, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank and Doring, *Tetrahedron* 44:60316040 (1988) (describing synthesis of various peptide sequences on cellulose disks); Fodor et al., Science, 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

The invention provides in vitro assays for identifying, in a high throughput format, compounds that can modulate the expression or activity of the polynucleotides or polypeptides of the invention. In a preferred embodiment, the methods of the invention include such a control reaction. For each of the assay formats described, "no modulator" control reactions that do not include a modulator provide a background level of binding activity.

In some assays it will be desirable to have positive controls to ensure that the components of the assays are working properly. At least two types of positive controls are appropriate. First, a known activator of a polynucleotide or polypeptide of the invention can be incubated with one sample of the assay, and the resulting increase in signal resulting from an increased expression level or activity of polynucleotide or polypeptide determined according to the methods herein. Second, a known inhibitor of a polynucleotide or polypeptide of the invention can be added, and the resulting decrease in signal for the expression or activity can be similarly detected.

D. Computer-Based Assays

Yet another assay for compounds that modulate the activity of a polypeptide or polynucleotide of the invention involves computer assisted drug design, in which a computer system is used to generate a three-dimensional structure of the polypeptide or polynucleotide based on the structural information encoded by its amino acid or nucleotide sequence. The input sequence interacts directly and actively with a pre-established algorithm in a computer program to yield secondary, tertiary, and quaternary structural models of the molecule. Similar analyses can be performed on potential receptors or binding partners of the polypeptides or polynucleotides of the invention. The models of the protein or nucleotide structure are then examined to identify regions of the structure that have the ability to bind, e.g., a polypeptide or polynucleotide of the invention. These regions are then used to identify polypeptides that bind to a polypeptide or polynucleotide of the invention.

The three-dimensional structural model of a protein is generated by entering protein amino acid sequences of at least 10 amino acid residues or corresponding nucleic acid sequences encoding a potential receptor into the computer system. The amino acid sequences encoded by the nucleic acid sequences provided herein represent the primary sequences or subsequences of the proteins, which encode the structural information of the proteins. At least 10 residues of an amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary, and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of a polypeptide or polynucleotide of the invention to identify binding sites of the polypeptide or polynucleotide of the invention. Binding affinity between the protein and ligands is determined using energy terms to determine which ligands have an enhanced probability of binding to the protein.

Computer systems are also used to screen for mutations, polymorphic variants, alleles and interspecies homologs of genes encoding a polypeptide or polynucleotide of the invention. Such mutations can be associated with disease states or genetic traits and can be used for diagnosis. As described above, GeneChip™ and related technology can also be used to screen for mutations, polymorphic variants, alleles and interspecies homologs. Once the variants are identified, diagnostic assays can be used to identify patients having such mutated genes. Identification of the mutated a polypeptide or polynucleotide of the invention involves receiving input of a first amino acid sequence of a polypeptide of the invention (or of a first nucleic acid sequence encoding a polypeptide of the invention), e.g., any amino acid sequence having at least 60%, optionally at least 70% or 85%, identity with the amino acid sequence of interest, or conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various polynucleotides of the invention, and mutations associated with disease states and genetic traits.

VII. Compositions, Kits and Integrated Systems

The invention provides compositions, kits and integrated systems for practicing the assays described herein using polypeptides or polynucleotides of the invention, antibodies specific for polypeptides or polynucleotides of the invention, etc.

The invention provides assay compositions for use in solid phase assays; such compositions can include, for example, one or more polynucleotides or polypeptides of the invention immobilized on a solid support, and a labeling reagent. For example, the kit could include an array consisting of a set or subset of the informative sequences listed in FIG. 1, FIGS. 5-8, or Tables 1-4. In each case, the assay compositions can also include additional reagents that are desirable for hybridization. Modulators of expression or activity of polynucleotides or polypeptides of the invention can also be included in the assay compositions.

The invention also provides kits for carrying out the therapeutic and diagnostic assays of the invention. The kits typically include a probe that comprises an antibody that specifically binds to polypeptides or polynucleotides of the invention, and a label for detecting the presence of the probe. The kits may include several polynucleotide sequences encoding polypeptides of the invention. Kits can include any of the compositions noted above, and optionally further include additional components such as instructions to practice a high-throughput method of assaying for an effect on expression of the genes encoding the polypeptides of the invention, or on activity of the polypeptides of the invention, one or more containers or compartments (e.g., to hold the probe, labels, or the like), a control modulator of the expression or activity of polypeptides of the invention, a robotic armature for mixing kit components or the like.

The invention also provides integrated systems for high-throughput screening of potential modulators for an effect on the expression or activity of the polypeptides of the invention. The systems typically include a robotic armature which transfers fluid from a source to a destination, a controller which controls the robotic armature, a label detector, a data storage unit which records label detection, and an assay component such as a microtiter dish comprising a well having a reaction mixture or a substrate comprising a fixed nucleic acid or immobilization moiety.

A number of robotic fluid transfer systems are available, or can easily be made from existing components. For example, a Zymate XP (Zymark Corporation; Hopkinton, Mass.) automated robot using a Microlab 2200 (Hamilton; Reno, Nev.) pipetting station can be used to transfer parallel samples to 96 well microtiter plates to set up several parallel simultaneous STAT binding assays.

Optical images viewed (and, optionally, recorded) by a camera or other recording device (e.g., a photodiode and data storage device) are optionally further processed in any of the embodiments herein, e.g., by digitizing the image and storing and analyzing the image on a computer. A variety of commercially available peripheral equipment and software is available for digitizing, storing and analyzing a digitized video or digitized optical image, e.g., using PC (Intel x86 or Pentium chip-compatible DOS®, OS2® WINDOWS®, WINDOWS NT®, WINDOWS95®, WINDOWS98®, or WINDOWS2000® based computers), MACINTOSH®, or UNIX® based (e.g., SUN® work station) computers.

One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g., by fluorescent or dark field microscopic techniques.

VIII. Administration and Pharmaceutical Compositions

Modulators of the polynucleotides or polypeptides of the invention (e.g., antagonists or agonists, such as FGF2, NCAM, peptide inhibitors of the FGF system, or siRNA and/or antisense inhibitors of genes which are overexpressed in subjects with mental disorders) can be administered directly to a mammalian subject for modulation of activity of those molecules in vivo. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

Diseases that can be treated include the following, which include the corresponding reference number from Morrison, *DSM-IV Made Easy,* 1995: Schizophrenia, Catatonic, Subchronic, (295.21); Schizophrenia, Catatonic, Chronic (295.22); Schizophrenia, Catatonic, Subchronic with Acute Exacerbation (295.23); Schizophrenia, Catatonic, Chronic with Acute Exacerbation (295.24); Schizophrenia, Catatonic, in Remission (295.55); Schizophrenia, Catatonic, Unspecified (295.20); Schizophrenia, Disorganized, Subchronic (295.11); Schizophrenia, Disorganized, Chronic (295.12); Schizophrenia, Disorganized, Subchronic with Acute Exacerbation (295.13); Schizophrenia, Disorganized, Chronic with Acute Exacerbation (295.14); Schizophrenia, Disorganized, in Remission (295.15); Schizophrenia, Disorganized, Unspecified (295.10); Schizophrenia, Paranoid, Subchronic (295.31); Schizophrenia, Paranoid, Chronic (295.32); Schizophrenia, Paranoid, Subchronic with Acute Exacerbation (295.33); Schizophrenia, Paranoid, Chronic with Acute Exacerbation (295.34); Schizophrenia, Paranoid, in Remission (295.35); Schizophrenia, Paranoid, Unspecified (295.30); Schizophrenia, Undifferentiated, Subchronic (295.91); Schizophrenia, Undifferentiated, Chronic (295.92); Schizophrenia, Undifferentiated, Subchronic with Acute Exacerbation (295.93); Schizophrenia, Undifferentiated, Chronic with Acute Exacerbation (295.94); Schizophrenia, Undifferentiated, in Remission (295.95); Schizophrenia, Undifferentiated, Unspecified (295.90); Schizophrenia, Residual, Subchronic (295.61); Schizophrenia, Residual, Chronic (295.62); Schizophrenia, Residual, Subchronic with Acute Exacerbation (295.63); Schizophrenia, Residual, Chronic with Acute Exacerbation (295.94); Schizophrenia, Residual; in Remission (295.65); Schizophrenia, Residual, Unspecified (295.60); Delusional (Paranoid) Disorder (297.10); Brief Reactive Psychosis (298.80); Schizophreniform Disorder (295.40); Schizoaffective Disorder (295.70); Induced Psychotic Disorder (297.30); Psychotic Disorder NOS (Atypical Psychosis) (298.90); Personality Disorders, Paranoid (301.00); Personality Disorders, Schizoid (301.20); Personality Disorders, Schizotypal (301.22); Personality Disorders, Antisocial (301.70); Personality Disorders, Borderline (301.83) and bipolar disorders, maniac, hypomaniac, dysthymic or cyclothymic disorders, substance-induced mood disorders, major depression, psychosis, including paranoid psychosis, catatonic psychosis, delusional psychosis, having schizoaffective disorder, and substance-induced psychotic disorder.

In some embodiments, modulators of polynucleotides or polypeptides of the invention can be combined with other drugs useful for treating mental disorders including useful for treating mood disorders, e.g., schizophrenia, bipolar disorders, or major depression. In some preferred embodiments, pharmaceutical compositions of the invention comprise a modulator of a polypeptide of polynucleotide of the invention combined with at least one of the compounds useful for treating schizophrenia, bipolar disorder, or major depression, e.g., such as those described in U.S. Pat. Nos. 6,297,262; 6,284,760; 6,284,771; 6,232,326; 6,187,752; 6,117,890; 6,239,162 or 6,166,008. In other embodiments, modulators or polypeptides of the invention, in particular FGF2, can be used to treat and/or prevent learning disabilities, memory loss, or disorders associated with learning disability and memory loss.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

The modulators (e.g., agonists or antagonists) of the expression or activity of the a polypeptide or polynucleotide of the invention, alone or in combination with other suitable components, can be made into aerosol formulations (i.e., they can be "nebulized") to be administered via inhalation or in compositions useful for injection. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to effect a beneficial response in the subject over time. The optimal dose level for any patient will depend on a variety of factors including the efficacy of the specific modulator employed, the age, body weight, physical activity, and diet of the patient, on a possible combination with other drugs, and on the severity of the mental disorder. The size of the dose also will be determined by the existence, nature, and extent of any adverse side effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side effects of the modulator at various concentrations, as applied to the mass and overall health of the subject. Administration can be accomplished via single or divided doses.

IX. Gene Therapy Applications

A variety of human diseases can be treated by therapeutic approaches that involve stably introducing a gene into a human cell such that the gene is transcribed and the gene product is produced in the cell. Diseases amenable to treatment by this approach include inherited diseases, including those in which the defect is in a single or multiple genes. Gene therapy is also useful for treatment of acquired diseases and other conditions. For discussions on the application of gene therapy towards the treatment of genetic as well as acquired diseases, see, Miller, *Nature* 357:455-460 (1992); and Mulligan, *Science* 260:926-932 (1993).

In the context of the present invention, gene therapy can be used for treating a variety of disorders and/or diseases in which the polynucleotides and polypeptides of the invention has been implicated. For example, compounds, including polynucleotides, can be identified by the methods of the present invention as effective in treating a mental disorder. Introduction by gene therapy of these polynucleotides can then be used to treat, e.g., mental disorders including mood disorders and psychotic disorders.

A. Vectors for Gene Delivery

For delivery to a cell or organism, the polynucleotides of the invention can be incorporated into a vector. Examples of vectors used for such purposes include expression plasmids capable of directing the expression of the nucleic acids in the target cell. In other instances, the vector is a viral vector system wherein the nucleic acids are incorporated into a viral genome that is capable of transfecting the target cell. In a preferred embodiment, the polynucleotides can be operably linked to expression and control sequences that can direct expression of the gene in the desired target host cells. Thus, one can achieve expression of the nucleic acid under appropriate conditions in the target cell.

B. Gene Delivery Systems

Viral vector systems useful in the expression of the nucleic acids include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the genes of interest are inserted into such vectors to allow packaging of the gene construct, typically with accompanying viral DNA, followed by infection of a sensitive host cell and expression of the gene of interest.

As used herein, "gene delivery system" refers to any means for the delivery of a nucleic acid of the invention to a target cell. In some embodiments of the invention, nucleic acids are conjugated to a cell receptor ligand for facilitated uptake (e.g., invagination of coated pits and internalization of the endosome) through an appropriate linking moiety, such as a DNA linking moiety (Wu et al., *J. Biol. Chem.* 263:14621-14624 (1988); WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acids of the invention can be modified by the addition of receptor ligands or antibodies specific for a receptor to permit receptor-mediated endocytosis into specific cells (see, e.g., WO 93/20221, WO 93/14188, and WO 94/06923). In some embodiments of the invention, the DNA constructs of the invention are linked to viral proteins, such as adenovirus particles, to facilitate endocytosis (Curiel et al., *Proc. Natl. Acad. Sci. U.S.A.* 88:8850-8854 (1991)). In other embodiments, molecular conjugates of the instant invention can include microtubule inhibitors (WO/9406922), synthetic peptides mimicking influenza virus hemagglutinin (Plank et al., *J. Biol. Chem.* 269:12918-12924 (1994)), and nuclear localization signals such as SV40 T antigen (WO93/19768).

Retroviral vectors are also useful for introducing the nucleic acids of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, a polypeptide or polynucleotide of the invention and thus restore the cells to a normal phenotype.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA*, 81:6349-6353 (1984); Danos and Mulligan *Proceedings of the National Academy of Sciences, USA*, 85:6460-6464 (1988); Eglitis et al. (1988), supra; and Miller (1990), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

In some embodiments of the invention, an antisense polynucleotide is administered which hybridizes to a gene encoding a polypeptide of the invention. The antisense polypeptide can be provided as an antisense oligonucleotide (see, e.g., Murayama et al., *Antisense Nucleic Acid Drug Dev.* 7:109-114 (1997)). Genes encoding an antisense nucleic acid can also be provided; such genes can be introduced into cells by methods known to those of skill in the art. For example, one can introduce an antisense nucleotide sequence in a viral vector, such as, for example, in hepatitis 13 virus (see, e.g., Ji et al., *J. Viral Hepat.* 4:167-173 (1997)), in adeno-associated virus (see, e.g., Xiao et al., *Brain Res.* 756:76-83 (1997)), or in other systems including, but not limited, to an HVJ (Sendai virus)-liposome gene delivery system (see, e.g., Kaneda et al., *Ann. NY Acad. Sci.* 811:299-308 (1997)), a "peptide vector" (see, e.g., Vidal et al., *CR Acad. Sci. III* 32:279-287 (1997)), as a gene in an episomal or plasmid vector (see, e.g., Cooper et al., *Proc. Natl. Acad. Sci. U.S.A.* 94:6450-6455 (1997), Yew et al. *Hum Gene Ther.* 8:575-584 (1997)), as a gene in a peptide-DNA aggregate (see, e.g., Niidome et al., *J. Biol. Chem.* 272:15307-15312 (1997)), as "naked DNA" (see, e.g., U.S. Pat. Nos. 5,580,859 and 5,589,466), in lipidic vector systems (see, e.g., Lee et al., *Crit Rev Ther Drug Carrier Syst.* 14:173-206 (1997)), polymer coated liposomes (U.S. Pat. Nos. 5,213,804 and 5,013,556), cationic liposomes (Epand et al., U.S. Pat. Nos. 5,283,185; 5,578,475; 5,279,833; and 5,334,761), gas filled microspheres (U.S. Pat. No. 5,542,935), ligand-targeted encapsulated macromolecules (U.S. Pat. Nos. 5,108,921; 5,521,291; 5,554,386; and 5,166,320).

Upregulated transcripts listed in the biomarker tables herein which are correlated with mental disorders may be targeted with one or more short interfering RNA (siRNA) sequences that hybridize to specific sequences in the target, as described above. Targeting of certain brain transcripts with siRNA in vivo has been reported, for example, by Zhang et al., *J. Gene. Med.*, 12:1039-45 (2003), who utilized monoclonal antibodies against the transferrin receptor to facilitate passage of liposome-encapsulated siRNA molecules through the blood brain barrier. Targeted siRNAs represent useful therapeutic compounds for attenuating the over-expressed transcripts that are associated with disease states, e.g., MDD, BP, and other mental disorders.

In another embodiment, conditional expression systems, such as those typified by the tet-regulated systems and the RU-486 system, can be used (see, e.g., Gossen & Bujard, *PNAS* 89:5547 (1992); Oligino et al., Gene Ther. 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These systems impart small molecule control on the expression of the target gene(s) of interest.

In another embodiment, stem cells engineered to express a transcript of interest can implanted into the brain.

C. Pharmaceutical Formulations

When used for pharmaceutical purposes, the vectors used for gene therapy are formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can additionally include a stabilizer, enhancer, or other pharmaceutically acceptable carriers or vehicles. A pharmaceutically acceptable carrier can contain a physiologically acceptable compound that acts, for example, to stabilize the nucleic acids of the invention and any associated vector. A physiologically acceptable compound can include, for example, carbohydrates, such as glucose, sucrose or dextrans; antioxidants, such as ascorbic acid or glutathione; chelating agents; low molecular weight proteins or other stabilizers or excipients. Other physiologically acceptable compounds include wetting agents, emulsifying agents, dispersing agents, or preservatives, which are particularly useful for preventing the growth or action of microorganisms. Various preservatives are well known and include, for example, phenol and ascorbic acid. Examples of carriers, stabilizers, or adjuvants can be found in *Remington's Pharmaceutical Sciences*, Mack Publishing Company, Philadelphia, Pa., 17th ed. (1985).

D. Administration of Formulations

The formulations of the invention can be delivered to any tissue or organ using any delivery method known to the ordinarily skilled artisan. In some embodiments of the invention, the nucleic acids of the invention are formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

E. Methods of Treatment

The gene therapy formulations of the invention are typically administered to a cell. The cell can be provided as part of a tissue, such as an epithelial membrane, or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the nucleic acids of the invention are introduced into cells by such methods as microinjection, calcium phosphate precipitation, liposome fusion, or biolistics. In further embodiments, the nucleic acids are taken up directly by the tissue of interest.

In some embodiments of the invention, the nucleic acids of the invention are administered ex vivo to cells or tissues explanted from a patient, then returned to the patient. Examples of ex vivo administration of therapeutic gene constructs include Nolta et al., *Proc Natl. Acad. Sci. USA* 93(6): 2414-9 (1996); Koc et al., *Seminars in Oncology* 23 (1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

X. Diagnosis of Mood Disorders and Psychotic Disorders

The present invention also provides methods of diagnosing mood disorders (such as major depression or bipolar disorder), psychotic disorders (such as schizophrenia), or a predisposition of at least some of the pathologies of such disorders. Diagnosis involves determining the level of a polypeptide or polynucleotide of the invention in a patient and then comparing the level to a baseline or range. Typically, the baseline value is representative of a polypeptide or polynucleotide of the invention in a healthy person not suffering from a mood disorder or a psychotic disorder or under the effects of medication or other drugs. Variation of levels of a polypeptide or polynucleotide of the invention from the baseline range (either up or down) indicates that the patient has a mood disorder or a psychotic disorder or at risk of developing at least some aspects of a mood disorder or a psychotic disorder. In some embodiments, the level of a polypeptide or polynucleotide of the invention are measured by taking a blood, urine or tissue sample from a patient and measuring the amount of a polypeptide or polynucleotide of the invention in the sample using any number of detection methods, such as those discussed herein.

Antibodies can be used in assays to detect differential protein expression in patient samples, e.g., ELISA assays, immunoprecipitation assays, and immunohistochemical assays. PCR assays can be used to detect expression levels of nucleic acids, as well as to discriminate between variants in genomic structure or transcription, such as the FGFR splice variants shown in FIG. 1 and described in the Examples.

In the case where absence of gene expression is associated with a disorder, the genomic structure of a gene can be evaluated with known methods such as PCR to detect deletion or insertion mutations associated with disease susceptibility. Conversely, the presence of mRNA or protein corresponding to a particular gene would indicate that an individual does not have the genetic mutation associated with the lack of gene expression or the associated disorder. Thus, diagnosis can be made by detecting the presence or absence of mRNA or protein, or by examining the genomic structure of the gene.

Single nucleotide polymorphism (SNP) analysis is also useful for detecting differences between alleles of the polynucleotides (e.g., genes) of the invention. SNPs linked to genes encoding polypeptides of the invention are useful, for instance, for diagnosis of diseases (e.g., mood disorders such as bipolar disease, major depression, and schizophrenia disorders) whose occurrence is linked to the gene sequences of the invention. For example, if an individual carries at least one SNP linked to a disease-associated allele of the gene sequences of the invention, the individual is likely predisposed for one or more of those diseases. If the individual is homozygous for a disease-linked SNP, the individual is particularly predisposed for occurrence of that disease. In some embodiments, the SNP associated with the gene sequences of the invention is located within 300,000; 200,000; 100,000; 75,000; 50,000; or 10,000 base pairs from the gene sequence.

Various real-time PCR methods can be used to detect SNPs, including, e.g., Taqman or molecular beacon-based assays (e.g., U.S. Pat. Nos. 5,210,015; 5,487,972; Tyagi et al., *Nature Biotechnology* 14:303 (1996); and PCT WO 95/13399 are useful to monitor for the presence of absence of a SNP. Additional SNP detection methods include, e.g., DNA sequencing, sequencing by hybridization, dot blotting, oligonucleotide array (DNA Chip) hybridization analysis, or are described in, e.g., U.S. Pat. No. 6,177,249; Landegren et al., *Genome Research,* 8:769-776 (1998); Botstein et al., *Am J Human Genetics* 32:314-331 (1980); Meyers et al., Methods in Enzymology 155:501-527 (1987); Keen et al., *Trends in Genetics* 7:5 (1991); Myers et al., *Science* 230:1242-1246 (1985); and Kwok et al., *Genomics* 23:138-144 (1994). PCR methods can also be used to detect deletion/insertion polymorphisms, such as the deletion polymorphism of the PSPHL gene associated with susceptibility to BP.

In some embodiments, the level of the enzymatic product of a polypeptide or polynucleotide of the invention is measured and compared to a baseline value of a healthy person or persons. Modulated levels of the product compared to the baseline indicates that the patient has a mood disorder or a psychotic disorder or is at risk of developing at least some aspects of a mood disorder or a psychotic disorder. Patient samples, for example, can be blood, urine or tissue samples. In some cases, one skilled in the art could use expression of genes in readily obtainable cells, e.g., lymphocytes, as a proxy for evaluation expression of those genes in one or more regions of the brain.

It is understood that the examples and embodiments described herein are for illustrative purposes only and that various modifications or changes in light thereof will be suggested to persons skilled in the art and are to be included within the spirit and purview of this application and scope of the appended claims.

Example 1

Differential Expression of Genes Associated with Suicide in Both BP and MDD Subjects Previous studies have investigated genes associated with mood disorders and suicidal tendencies, using microarrays and PCRs to analzye gene expression (Sibille et al., 2004; Yanagi M, et al., *J Hum Genet.,* 50(4):210-6 (2005)). Neither investigation, however, used a stringent analysis of suicide compared to mood disorder and suicide compared to controls to detect genes that might be most representative of suicide. This Example describes microarray gene expression profiles in the amygdala, anterior cingulate, and cerebellum in postmortem brains from BPD and MDD patients that committed suicide, focusing on mRNA expression levels of the molecules which regulate white-matter, oligodendrocyte, myelin, and other pathways. The genes identified here may be used as biomarkers for detecting and treating suicidal behavior.

Genes were discovered by selecting subjects run on U133P chips with mRNA quality>1.4, pH>6.6, and AFS=0. Suicide victims with a mood disorder (n=14) were compared to non-suicide victims suffering from a mood disorder (n=9) and controls (n=27). The age and pH were different between groups, and were entered as a covariate in ANCOVA. Myelin and oligodendrocyte gene expression were found to be dysregulated in suicidal mood disorder subjects compared to non-suicidal mood disorder subjects or controls in the amygdala. The complete list of identified genes which were dysregulated in suicidal patients versus non-suicidal mood disorder patients is presented in Table 1A. Table 1B lists genes which were dysregulated in suicidal MDD patients versus non-suicidal MDD patients, and genes which were dysregulated in suicidal MDD patients versus control patients.

A similar study was performed using brains of MDD subjects who were known to be drug abusers and comparing gene expression in those subjects to gene expression in MDD subjects who were not substance abusers, as well as to control subjects. Table 1C is a list of genes which were shown to be dysregulated in substance-abusing MDD patients versus MDD patients who were not substance abusers. Table 1C also shows genes which were dysregulated in substance-abusing MDD patients versus control subjects.

In a related study, two cohorts were used to study and compare gene expression in BP and MDD patients versus normal patients. Cohort A consisted of 7 controls, 6 BPD patients, and 9 MDD patients. Cohort B included 7 controls and 5 MDD patients. The subjects were selected to avoid possible confounding effects of agonal events, tissue pH, RNA integrity, gender and age. The results, summarized in FIGS. 5-8, show that changes were observed in the expression levels of GPCRs and molecules regulating cAMP- and phosphatidylinositol signaling pathways in the cerebral cortices, especially in the anterior cingulate cortex, of mood disorder patients. Expression levels of molecules acting as negative regulators in cAMP signaling were increased in BPD, while molecules activating cAMP signaling were not altered. Contrasted with the changes in BPD, molecules suppressing cAMP signaling were decreased in MDD. Expression levels of inositol polyphosphate-1-phosphatase and phosphatidylinositol 3-kinases were altered in BPD, while protein kinase C beta-1, inositol triphosphate receptor-1, inositol polyphosphate-5-phosphatase were increased in MDD. Two orphan GPCR genes, GPRC5B and GPR37, consistently showed significant decreases in the three cortices in MDD, and significant increases in anterior cingulate cortex of BPD. Measuring differences in the expression of the genes identified in FIGS. 5-8 is a useful tool for determining whether a subject is suffering from a particular mental illness, particularly BP or MDD.

Example 2

Identification of Lithium Responsive Genes which are Dysregulated in BPD

This Example demonstrates that certain genes in non-human primates (healthy rhesus macaque monkey) are differentially expressed in response to treatment with the mood-stabilizing drug, lithium (Li), the drug of choice for the treatment of BP. Gene expression profiling was carried out on the anterior cingulate cortex (AnCg), dorsolateral prefrontal cortex (DLPFC), hippocampus (HC) and amygdala (AMY) of rhesus macaque monkeys, using the gene expression detection methods described herein, and compared to the human postmortem results described above. Table 2A shows the lithium-responsive genes which had been previously identified in the literature and which were confirmed by the present investigation. Table 2B shows genes that are newly identified as lithium-responsive in primates and which are also dysregulated in human subjects with bipolar disorder.

Example 3

FGFR2 Variant Differences in Mood Disorders

The FGF receptor 2 (FGFR2) transcript is consistently found to be decreased in several brain areas of depressed subjects (see, e.g., U.S. patent application Ser. No. 10/701,263, filed Nov. 3, 2003, published as U.S. Pat. Publ. No. 20040152111-A1 on Aug. 5, 2004). The human FGFR2 gene contains 19 exons and produces as many as 13 splice variants. These variants fall into three main functional classes: first, variants that lack the transmembrane and tyrosine kinase domain which are thought to be soluble receptors; second, variants that contain the Ig IIIc type domain encoded by exon 9; and third, variants that contain the Ig IIIb type domain encoded by exon 8. The Ig III type domain confers ligand specificity and thus these latter two variants have different pharmacological profiles based on their use of the IIIc or IIIb domain. This Example describes PCR-based measurements of exons present in total RNA derived from human cortex (dorsolateral prefrontal and anterior cingulated) and hippocampus. Methods Post-mortem human brains were obtained and dissected as previously described (Evans et al., *PNAS* 101(43):15506-11 (2004)). RNA for microarray analysis and semi-quantitative RT-PCR was extracted from discrete brain regions using Trizol.

Microarray data was generated with a combination of Affymetrix 133A anti 133plus 2.0 chips and was analyzed using a custom probe mapping file based on a recent generation of the RefSeq database (http://brainarray.mbni.med.umich.edu/Brainarray/Database/CustomCDF). Each biological sample was run independently at two sites (University of California-Irvine, University of run California-Davis or the University of Michigan). Probe set signals were calculated using RMA (Bolstad et al., *Bioinformatics* 19(2):185-93 (2003)) and statistical comparisons were made after median centering the RMA data separately for each technical block (across independent cohorts and sites). P-values were constructed from t-tests between cases and controls. The final subject composition included 13 major depressive subjects and 16 controls. All were free of agonal factors, had brain pH measurements greater than 6.8, and met other quality measures.

Semi-quantitative RT-PCR data were generated with exon specific primers and the SVBR green method using the Bio-Rad iCycler. All primer pairs used in quantitative reactions were tested for efficiency and determined to be at approximately 100%. Cycle threshold (Ct) values were chosen within the linear range of amplification and were normalized to total cDNA concentration as determined by the PicoGreen assay (Molecular Probes). Contaminating genomic DNA was eliminated with DNAse prior to cDNA synthesis with a mixture of random hexamers and poly-T primers and was confirmed eliminated by amplifying fragments across smaller introns (axon 3 to exon 4 and exon 7 to exon 10). No intron-containing amplicons were detected.

Results

The results of the above-mentioned study are partially summarized in FIG. 1, which shows the differential expression of exons 5 and 11 in depressed versus control subjects. More specifically, the results show that the ratio of expression of exon 5 to exon 11 is significantly lowered in MDD patients, particularly in the DLPFC region. A similar analysis of the expression of exon 9 (coding for the IIIc variant) showed that exon 9 expression in the AnCg and HC regions was decreased in MDD subjects.

Example 4

Effect of Injection of FGF2, FGL Peptide (NCAM), and Peptide Inhibitor of FGF Receptors on the Behavior of Rodents A. Microinjection of FGF2

Figure 2:
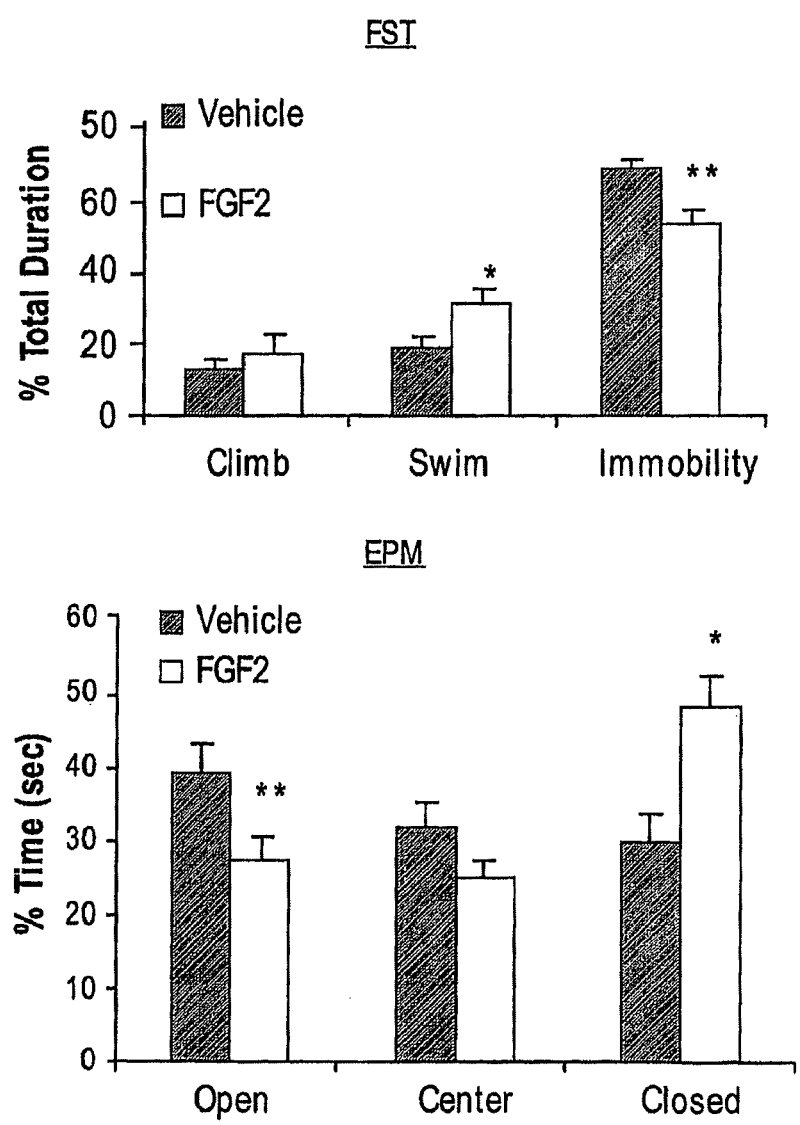
FIG. 2 shows the effect of acute injection of FGF2 on mouse depression and anxiety, as measured by mobility tests (top) and the elevated plus maze (EPM) test (bottom), respectively. "Open," "center," and "closed" refer to time spent in the open, center and closed parts of the EPM, respectively.

This set of experiments shows significant effects following the microinjection of FGF2, using both the forced swim test (FST) and the elevated plus maze (EPM) to evaluate depression in the subject animals. In the FST, the FGF2-injected (n=12) animals exhibited more swimming (t[23]=2.20, p<0.05) and less immobility (t[23]=2.88, p<0.01) than controls (n=13). This is indicative of less depression-like behavior in FGF2 animals. However, in the EPM, the FGF2-injected animals spent significantly more time in the closed arms (t[13]=3.18, p<0.01) and less time in the open arms (t[13]=2.46, p<0.05). These results (FIG. 2) show that anxiety-like behavior is increased after an acute injection of FGF2.

B. Microinjection of NCAM (FGL Peptide)

Figure 3:
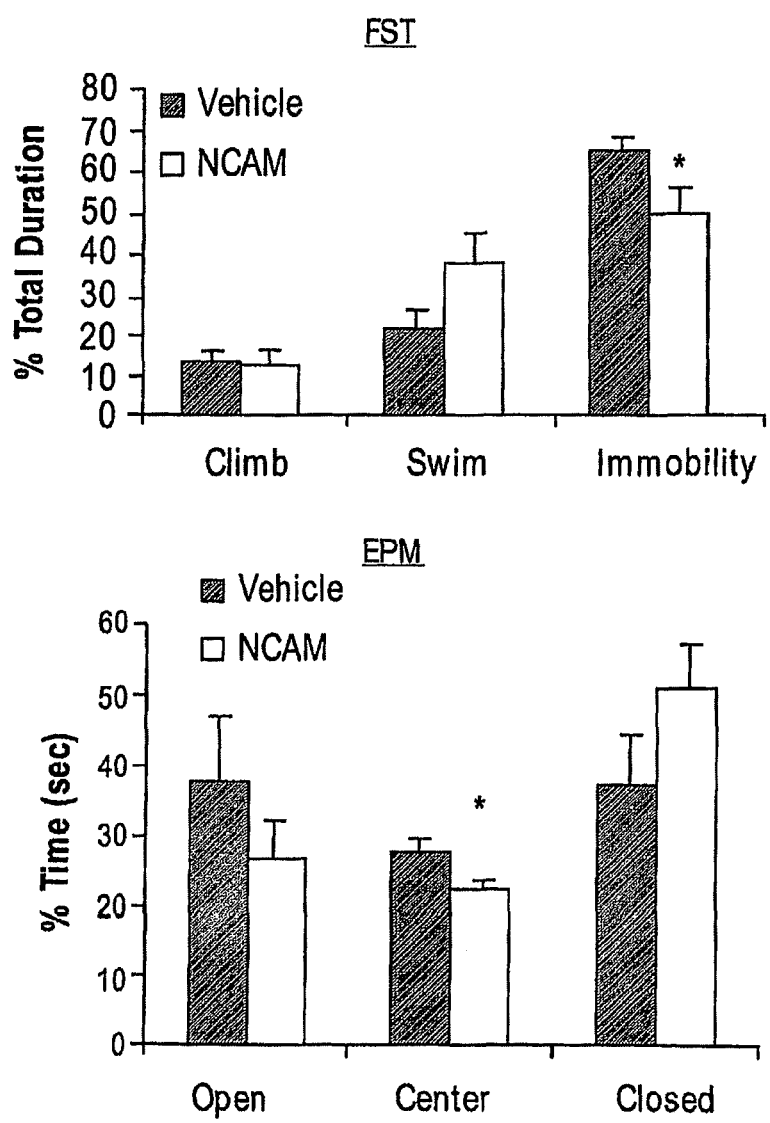
FIG. 3 shows the effects of injections of NCAM peptide on mouse depression and anxiety, as measured by the climbing and forced swim test (top) and the elevated plus maze (EPM) test (bottom), respectively. "Open," "center," and "closed" refer to time spent in the open, center and closed parts of the EPM, respectively.

This set of experiments shows a significant effect on animal mood in the forced swim test after NCAM administration (amino acid sequence=EVYVVAENQQGKSKA (SEQ ID NO:34); see FIG. 3). Here, the NCAM-injected animals (n=13) exhibited less immobility (t [24]=2.13, p<0.05) than controls (n=13). Again, this is an index of less depression-like behavior. This is also in the same direction as the FGF2 data, consistent with the fact that both FGF2 and NCAM interact with the FGF receptor. Similarly, the NCAM-injected animals spent more time (although not significantly more time) in the closed arms and less time in the open arms, consistent with increased anxiety-like behavior. NCAM-injected animals also spent significantly less time in the center quadrant (t[18]=2.40, p<0.05).

C. Microinjection of a Peptide Inhibitor of FGFR

This set of experiments shows a significant effect on animal mood, using both the forced swim test and the elevated plus maze test, after injection with an FGF system peptide inhibitor (amino acid sequence=HFKDPKRLY; SEQ ID NO:35). The results are shown in FIG. 4. In the FST, the inhibitor-injected animals (n=7) exhibited significantly less climbing (t[12]=2.06, p<0.05), less swimming (t[12]=1.92, p<0.05) and more immobility (t[12]=3.58, p<0.005) than controls (n=7). These results show that inhibition of the FGF system can result in increased depression-like behavior. These results confirm and advance the results of the previous data sets, and are consistent with studies of the postmortem tissue of individuals with major depression. The inhibitor-injected animals also spent significantly more time in the center quadrant of the EPM (T[7,7]=35.0, p=0.03). Although the same animals spent less time in the closed arms and equal time in the open arms, indicative of increased anxiety-like behavior, the lengths of time spent were not significantly different. These observations are nevertheless consistent with the conclusions drawn from the microinjection studies above.

D. Administration of FGF2 Induces Long-Term Changes in Hippocampal Gene Expression Methods.

Sprague-Dawley rats were injected with either vehicle or FGF2 (20 ng/g, s.c.) the day after birth and sacrificed after Morris water maze testing as adults. We assessed changes in gene expression using both a candidate approach and a gene discovery approach with laser-capture microdissection of the dentate gyrus followed by microarray analyses.

Results.

Rats injected with FGF2 performed significantly better in learning and memory tests (e.g., 20 seconds on average to find a hidden platform in Morris Water maze test versus 25 seconds on average for vehicle-injected rats). Several genes associated with neural plasticity were also found altered in the adult rats, as shown by histochemical and RNA expression assays. For example, expression of GAP-43, Rgs4, trkB, CCK, SST, and Vgf was increased, while expression of NCAM was decreased.

Example 5

Anxiolytic Effect of Chronically Administered FGF2

Anxiety disorders have a high comorbidity with other neuropsychiatric disorders including Major Depression (MD). This Example shows that chronic FGF2 administration has an anxiolytic effect in rats. Rats were placed into "high anxiety" (LR) or "low anxiety" (HR) groups based on their behavior in a variety of motor and behavioral tests. Both groups of animals were administered either FGF2 (5 ng/g) or vehicle by intraperitoneal injection every 48 hours for 3 weeks. One day after the last FGF2 injection, all animals were tested in the elevated plus-maze (EPM) and light-dark (LD) anxiety test.

The apparatus for the EPM test is constructed of black Plexiglass with four elevated open arms (70 cm from the floor, 45 cm long, and 12 cm wide). Illumination is provided by a 40-watt desk lamp facing a wall and placed behind one of the closed arms. The scientists put the animal inside the system. Animals that are less anxious spend more time in the open arms whereas animals that are more anxious spend less time in the open arms.

The LD test is conducted in a 30×60×30-cm Plexiglas shuttle box with a translucent cover. Each box is divided into two equal-sized compartments by a wall with a 12 cm-wide open door. One compartment is painted white and brightly illuminated, and the other is painted black with very dim light. The time each rat spends in each compartment is monitored by rows of five photocells located 2.5 cm above the grid floor of each compartment. Animals that are less anxious spend more time in the light compartment.

Figure 9:
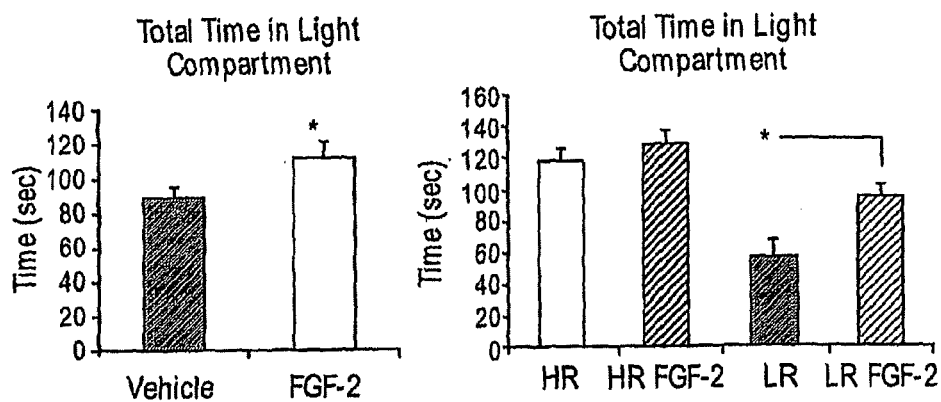
FIG. 9 shows two charts which illustrate the effect of chronic FGF-2 administration (5 ng/g, 3 weeks) on anxiety in rodents with different, as measured by the time the rodents spend in the light compartment of the test system. LR, animals with intrinsic high anxiety; HR, animals with intrinsic low anxiety; HRFGR-2, low anxiety animals administered FGF-2; LRFGF-2, high anxiety animals administered FGF-2.

The results show that animals who received chronically administered FGF2 are less anxious than animals who receive vehicle (FIG. 9, top). The anxiety-reducing effects of FGF2 are clearly more pronounced in rats who are inately more anxious (LR) prior to the FGF2 regimen (FIG. 9, top).

Figure 10:
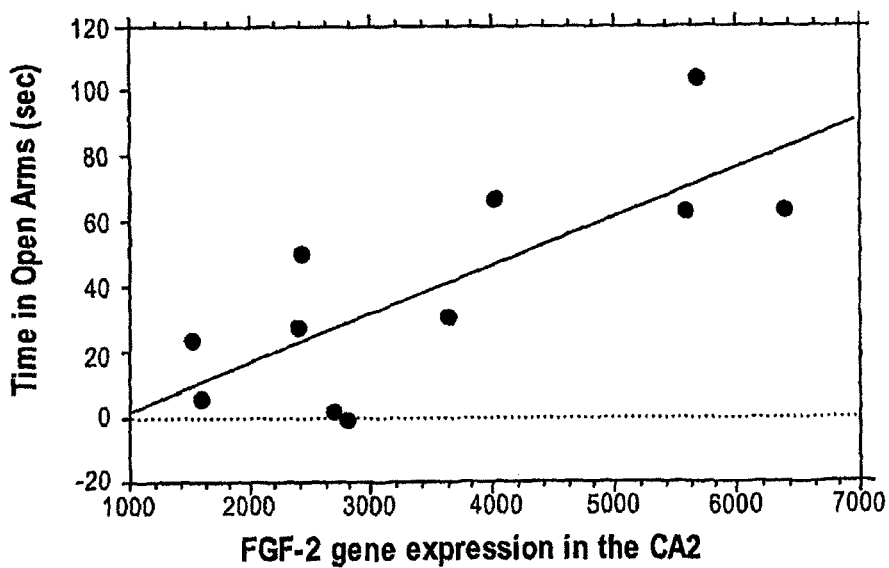
FIG. 10 shows the inverse relationship between FGF-2 gene expression and anxiety behavior using the "open arms" test. CA-2, hippocampus region CA-2.

To further understand the relationship between FGF2 expression and anxiety, FGF2 expression was measured in the CA-2 region of the hippocampus of rat brains taken from rats which exhibited varying levels of anxiety (as measured by the EPM test). The results (FIG. 10) show that FGF2 levels are inversely related to anxiety, i.e., higher levels of inate FGF2 expression in rats correlate with lower levels of anxiety.

Taken as a whole, the Example shows that chronic FGF2 administration is useful for alleviating symptoms of anxiety in anxious animals and in subjects who are suffering from disorders such as MDD which are associated with anxiety. The data also shows that detection of FGF2 levels is useful for diagnosing anxiety or characterizing disorders associated with anxiety, such as Major Depression Disorder.

Example 6

Differential Regulation of FGFR Splice Variants Associated with Chronic Stress

In the adult CNS, fibroblast growth factor receptor 2 (FGFR2) and fibroblast growth factor receptor 3 (FGFR3) are differentially distributed. The mRNA of these receptors undergoes alternative splicing in the exons coding for the carboxyl terminus of the Ig-like domain III. This mutually exclusive mRNA splicing produces two isoforms of FGFR2 and FGFR3 with significantly different ligand binding profiles: one isoform expressing exon IIIb (FGFR2b/FGFR3b), and one isoform expressing exon IIIc (FGFR2c/FGFR3c). Exon selection is strictly tissue-dependent during development with exon IIIb expressed in epithelial lineages and exon IIIc expressed in mesenchymal lineages. Cell cycle-dependent IIIb to IIIc switches, however, have been induced in vitro by the exogenous addition of FGF1 and FGF2. This Example shows that chronic stress induces a decrease in the FGFR2 exon IIIc:IIIb splice variant expression ratio.

Animals.

Twenty-four male Sprague-Dawley rats weighing 220-250 g were ordered from Charles River (Wilmington, Mass.) and remained undisturbed for one week to acclimatize to housing conditions. The animals were housed in pairs on a 12 h light-dark cycle (lights on 6:00 A.M.) with food and water available ad libitum. All experiments were conducted in accordance with the NIH Guide for the Care and Use of Animals and the University Committee on the Use and Care of Animals.

FGF2 Injection Treatments and Chronic Unpredictable Stress (CUS) Conditions.

Half of the rats (n=12) were administered vehicle (0.1M PBS with 100 μg/mL bovine serum albumin), and the other half (n=12) were administered human recombinant FGF2 dissolved in vehicle in 5 ng/g dosages (Sigma, St. Louis, Mo.) every 48 hours for three weeks. All treatments were injected intra-peritoneally. During the same three week period as the FGF2 treatments, the vehicle group was either handled (n=6) or exposed to CUS (n=6). Likewise, the FGF2 injected group was either handled (n=6) or exposed to CUS (n=6). The animals were exposed to the following chronic unpredictable stressors (described in Isgor et al. (2004)): ether (30 s), cold (2 h), noise (15 m), isolation (24 h), or restraint (2 h). The stressors were randomized to avoid habituation; sessions occurred once each clay in either the morning or afternoon. The 2×2 (condition by treatment) design divided the subjects into nonstressed/vehicle (NS/V), nonstressed/FGF2 injection (NS/F), stressed/vehicle (SN), and stressed/FGF2 injection (S/F) groups.

Forced Swim Testing.

To test for possible FGF2 injection effects on anti-depressant behavior for other studies, all animals were subjected to forced swim testing according to Lucid (1997) 24 h after the termination of the FGF2 treatments and CUS conditions.

Brains.

The rats were sacrificed by the faculty by decapitation three days after termination of the forced swim testing. Brains were then removed and snap frozen in isopentane at −80° C.

Total RNA Extraction.

Gross dissections were performed on the frontal cortex of all brains. Total RNA extraction was executed following the reagent manufacturers' instructions. Tissues were homogenized in TRIzol (Invitrogen, Carlsbad, Calif.; monophasic phenol and guanidine isothiocyanate). Phase separation and RNA precipitation were carried out with chloroform and 2-propanol followed by centrifugation. RNA samples were purified using the RNeasy Mini Kit (Qiagen, Valencia, Calif.), repeatedly washing samples through spin columns. Pure RNA samples were reconstituted with RNase-free water, followed by an integrity analysis for 28s/18s ribosomal RNA peaks with the 2100 Bioanalyzer and LabChip (Agilent Technologies, Palo Alto, Calif.) system. Using the Bioanalyzer's concentration readings, the samples were normalized to 25 ng/µL of total RNA per subject and stored at −80° C.

cDNA Synthesis.

cDNA was synthesized using the iScript cDNA Synthesis Kit (Bio-Rad, Hercules, Calif.). All 24 RNA samples were reversed transcribed with iScript Reverse Transcriptase (Bio-Rad) and primed with oligo (dT) and random hexamer primers. Reaction mixes were incubated in an iCycler PCR unit (Bio-Rad) according to the manufacturer's standard 40 min protocol. The double-stranded cDNA solutions were then analyzed for quality and concentration using Invitrogen's Quant-iT PicoGreen dsDNA kit. 10-fold serial dilutions were prepared with 2 µg/mL (high range) and 50 ng/mL (low range) stock DNA to generate standard curves. The fluorescently labeled samples were analyzed with a 1420 Victor$^2$ Multilabel Counter (EG&G Wallac, Wellesley, Mass.) using the basic Fluorescein protocol. Total cDNA samples were further normalized to fit the linear regression of the high range standard curve.

Real Time RT-PCR Primer Design.

Sequences for rat FGFR2 and FGFR3 exons were obtained from NCBI's Entrez Gene database (www.ncbi.nlm.nih.gov) and the Ensembl-Rat gene database (www.ensembl.org). Exon sequences were analyzed using NCBI's nucleotide and protein BLAST and were matched with their corresponding protein products within the receptor structures (FIG. 11). FGFR2 and FGFR3 exon sequences were analyzed for secondary structure using the Mfold nucleic acid folding web server. Probable hairpin regions were noted for exclusion in primer design. Optimized primer sequences (FIG. 11) were generated using the Primer3 web-based software. All primers were 18-22 base pairs, targeted amplicons of 75-150 bps, and purchased from Invitrogen's Custom Primer Synthesis service. The primer sequences (50 nmol/mL) were validated and tested for efficiency with 5-fold serial dilutions of pooled cDNA using iQ SYBR Green detection on an iCycler iQ Real Time RT-PCR unit (Bio-Rad).

Real Time RT-PCR Quantification.

Real time reverse-transcriptase-PCR (RT-PCR) amplification reactions were performed to quantify relative abundances of mRNA (reverse transcribed to cDNA) of selected FGFR2 and R3 exons in each of the four treatment by condition groups (n=6). iQ SYBR Green Supermix detection was used on an iCycler iQ Real Time RT-PCR system (Bio-Rad) according to the manufacturer's recommendations, with the exception of preparing 19 µL reactions instead of the instructed 50 µL. Reference genes were omitted because total cDNA pools were normalized. Reactions were run in duplicates, increasing each group size to n=12. Two exons in juxtaposition were amplified per plate for relative comparison (emphasis placed on exon IIIb and exon IIIc). Reaction wells were arranged to equalize positional representation amongst all groups. PCR protocol was as follows: hot start at 95° C. for 30 s, followed by 40 cycles of denature at 95° C. for 15 s, annealing at 60° C. for 15 s, and elongation at 72° C. for 15 s. Florescence was quantified after every cycle, and melt curve analysis was performed following amplification to ensure single product reactions. Thorough methodology is described by Kerman et al. (2006).

Data Analysis

Real time RT-PCR data was output as threshold cycle (Ct) values, using Bio-Rad's iCycler iQ software's algorithm to calculate the optimum fluorescence thresholds for reliable detection (the mean florescence value of the first ten PCR cycles plus 10 standard deviations). Essentially, lower Ct values indicate higher amounts of initial target cDNA because fewer PCR cycles are required to reach fluorescence thresholds. Ct values for all reactions were then grouped and presented as means with standard errors. Sample sizes were 9-12 per group due to outlier (≥2 StDev from mean) exclusion. Mean fold changes were calculated using a $2^{\Delta Ct}$ method (modification of technique described by Livak and Schmittgen (2001)), comparing mean Ct values within one variable (treatment effects within one condition or condition effects within one treatment). This $2^{\Delta Ct}$ method assumes equal primer efficiencies; however, for the purposes of quantifying relative expression, it is acceptable if the primers are validated. Exon IIIc to exon IIIb ratios were determined by calculating individual $2^{\Delta Ct}$ values between corresponding reactions of the two exons. Ratios were sorted similarly to the Ct value groups and presented as mean ratios with standard errors. Statistical significance tests for differences in multiple exon mean Ct values and individual ratios were performed using two-factor ANOVA and Student's t-test for each comparison variable. Significance level was set as p<0.05. All statistical analysis was done in Microsoft Excel 2003.

Results.

Chronic stress induced significant decreases in the exon IIIc to exon IIIb (mutually exclusive expression) splice variant ratio in the vehicle group (P<0.00004) and in the FGF2 injection group (P<0.005) (FIG. 12). While exon IIIc expression remained relatively higher than IIIb in all groups, IIIb expression increased significantly with stress while IIIc expression changed only slightly. Thus, stress increases expression of the IIIb variant relative to the IIIc variant for both FGFR2 and FGFR3. FGF2 injection did not alter the IIIc:IIIb ratio significantly in either the NS or S group (P>0.1), nor did it significantly affect the magnitude of ratio changes caused by stress.

The results show that the affinity of FGFR2 or FGFR3 for endogenous ligands such as FGF2 and FGF9 (which are differentially expressed in MDD subjects) or for exogenous ligands (e.g., pharmacological peptides or other compounds) can be altered by stress. The invention described herein provides methods of detecting variations in FGFR2 and FGFR3 splicing and modifying subject care accordingly. In another embodiment, the invention provides methods for identifying and optimizing therapeutics for treating depression and related ailments.

Example 7

Differential Regulation of Genes in the Locus Coeruleus and the Dorsal Raphe in Subjects with Bipolar and Major Depression Disorder The Locus Coeruleus (LC) and the Dorsal Raphe (DR) are the major sources for noradrenergic and serotonergic innervation of the brain respectively. Dysregulation of these neurotransmitters has been implicated in psychiatric disorders. This Example uses postmortem brains of patients with MDD (N=12), BPD (N=6), and healthy subjects (N=9) to contrast gene expression profiles in the LC and DR regions of their brains. All subjects met inclusion criteria of brain pH>6.6 and zero agonal factors. Total RNA samples from laser capture microdissected LC and DR samples were extracted, amplified, and probed with Affymetrix high density oligonucleotide microarrays. Gene expression data were analyzed by ANOVA of robust multichip average algorithm (p≤0.1) and by MAS5.0 "present" call algorithm (min. of 50% presences in one of the 3 health states). Genes meeting these criteria were analyzed using Ingenuity Pathway Analysis (IPA). Compared to healthy individuals, 774 and 636 genes show altered expression in the LC and 627 and 656 genes show altered expression in the DR of MDD and BPD patients, respectively.

LC Gene Expression Patterns:

The data is summarized in Table 3. Ingenuity Pathway Analysis revealed that 10 genes of the glutamate receptor signaling pathway are significantly altered in MDD (p<0.01) but not in BPD. Glutamate signaling gene expression alterations are present in following synaptic compartments of the locus coeruleus: glial cells, presynaptic neurons, and postsynaptic neurons. This shows that glutamate signaling is altered in LC of MDD patients. Glial transporters, glutamine synthetase, AMPA, kainate, GRM1 and GRM7 are thus targets for treating glutamatergic imbalance.

The expression of genes related to growth, i.e., fibroblast growth factors, are also significantly altered in the LC of MDD patients. Drugs that target FGFR3, TrkB receptor, growth hormone receptor, or which mimic the actions of FGF-2, would increase neurite outgrowth in the LC and reserve neuronal loss.

Genes that are almost exclusively expressed in glia are significantly downregulated. These genes are useful markers for global glial alterations in MDD patients.

DR Gene Expression Patterns.

The data is summarized in Table 4. IPA analyses of the DR revealed alterations in the expression of a number of genes in growth factor-related pathways in MDD. Expression of most of the altered genes was downregulated. Likewise, the expression of a number of genes in growth factor-related pathways was downregulated in samples from the BP cohort. However, these genes were distinct from those detected in the MDD cohort. Several genes that were common to both disorders were identified; their expression was altered in the same direction in MDD and BPD subjects.

All publications, databases, Genbank sequences, patents, and patent applications cited herein are hereby incorporated by reference.

What is claimed is:

1. A method for treating a major depressive disorder (MDD) in a subject, the method comprising administering a therapeutically effective amount of a ligand comprising an FG loop (FGL) peptide derived from NCAM to the subject, wherein the ligand activates fibroblast growth factor (FGF) receptor and is an NCAM peptide mimetic.

2. The method of claim 1, wherein the subject has been diagnosed with MDD.

3. The method of claim 1, wherein the MDD is associated with anxiety.

4. The method of claim 1, wherein the MDD involves a persistent sad, anxious, or empty mood.

5. The method of claim 1, wherein the ligand is administered with a pharmaceutically acceptable carrier.

6. The method of claim 1, wherein the ligand is administered orally, nasally, topically, intravenously, intraperitoneally, intrathecally, or intracerebroventricularly.

7. The method of claim 1, wherein the subject is a human.

8. The method of claim 1, wherein the FGL peptide comprises SEQ ID NO:34.

9. The method of claim 1, wherein the ligand is linked to a dimerization compound.

10. The method of claim 1, wherein the ligand is administered at a dose of about 1 ng/kg to 10 mg/kg.

11. The method of claim 1, wherein the ligand comprises a —COCH$_2$— linkage.

* * * * *